United States Patent
Alam et al.

(10) Patent No.: US 9,488,562 B1
(45) Date of Patent: Nov. 8, 2016

(54) MEASUREMENT OF DYNAMIC BATTERY PACK PROPERTIES

(71) Applicant: Amazon Technologies, Inc., Seattle, WA (US)

(72) Inventors: Mohammed Aftab Alam, San Jose, CA (US); Ramez Nachman, Seattle, WA (US); John Douglas Porter, San Francisco, CA (US)

(73) Assignee: Amazon Technologies, Inc., Seattle, WA (US)

( * ) Notice: Subject to any disclaimer, the term of this patent is extended or adjusted under 35 U.S.C. 154(b) by 73 days.

(21) Appl. No.: 14/642,716

(22) Filed: Mar. 9, 2015

(51) Int. Cl.
*G01N 3/303* (2006.01)
*G01L 5/00* (2006.01)

(52) U.S. Cl.
CPC ............. *G01N 3/303* (2013.01); *G01L 5/0052* (2013.01)

(58) Field of Classification Search
None
See application file for complete search history.

(56) References Cited

U.S. PATENT DOCUMENTS

| | | | | |
|---|---|---|---|---|
| 2,755,658 A | * | 7/1956 | Brown | G01P 21/00 73/12.13 |
| 4,763,529 A | * | 8/1988 | Leonard | G01N 3/20 73/851 |
| 7,544,444 B2 | * | 6/2009 | Adachi | H01M 2/16 429/247 |
| 2009/0146663 A1 | * | 6/2009 | Takeno | H01M 10/486 324/426 |

\* cited by examiner

*Primary Examiner* — Robert R Raevis
(74) *Attorney, Agent, or Firm* — Lee & Hayes, PLLC

(57) ABSTRACT

An example method includes positioning a mass at a height opposite a modulator characterized by a particular strain rate and support by a carrier moveably disposed opposite the mass. The method also includes releasing the mass such that the mass impacts the modulator, and an additional component connected to the carrier causes failure of a sample of material. The method further includes determining a displacement of the carrier corresponding to failure of the sample, determining a force applied to the modulator by the mass and resulting in failure of the sample, and determining at least one of a dynamic strength of the sample and a dynamic modulus of the sample. In such a method, the dynamic strength is based on the force applied to the modulator and the strain rate. Additionally, the dynamic modulus is based on the displacement of the carrier and the strain rate.

20 Claims, 8 Drawing Sheets

MEASUREMENT OF DYNAMIC BATTERY PACK PROPERTIES

BACKGROUND

Electronic book readers, tablet computers, wireless telephones, laptop computers, and other electronic devices often experience relatively high dynamic loads when such devices are accidentally dropped or otherwise mishandled by users. As a result, it may be desirable to manufacture such electronic devices using materials capable of withstanding such dynamic events reliably and without failure. The dynamic strength, dynamic modulus, and/or other dynamic properties of some of the materials commonly used to manufacture such devices may be relatively easily determined through testing. For instance, plastics, metals, and other materials may be formed into a "dog bone" shape or other similar shape enabling a sample of such materials to be subjected to both static and dynamic testing using existing testing systems. However, it may be difficult to determine such properties for glass or other device materials that are relatively brittle and/or that are not easily formed into shapes suitable for known testing systems. Additionally, existing testing systems may not be acceptable for use in evaluating device materials that are potentially combustible, potentially toxic, and/or otherwise potentially dangerous when subjected to dynamic loads.

BRIEF DESCRIPTION OF THE DRAWINGS

The detailed description is described with reference to the accompanying figures. In the figures, the left-most digit(s) of a reference number identifies the figure in which the reference number first appears. The same reference numbers in different figures indicate similar or identical items.

DETAILED DESCRIPTION

Figure 1:
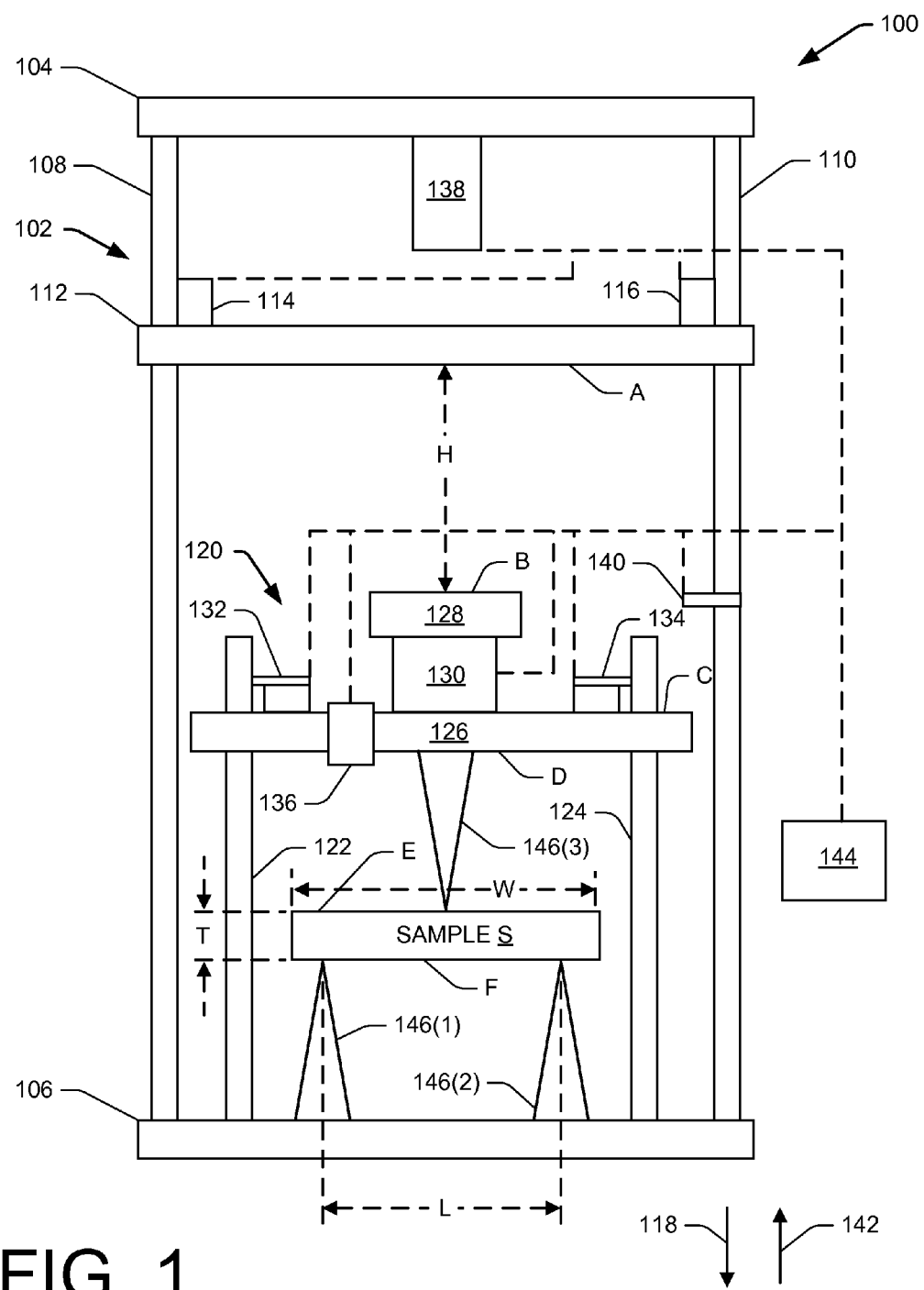
FIG. 1 illustrates an example system for determining one or more dynamic properties of a sample.

Described herein are systems and methods for determining one or more dynamic properties of a sample of material. In example embodiments of the present disclosure, a testing system may be employed to provide a dynamic load to such a sample, thereby causing failure of the sample. The example systems of the present disclosure may be configured to measure the displacement of various system components as well as the dynamic force applied to the sample. The systems may also enable the application of such force at a predetermined strain rate. As a result, the example systems of the present disclosure may facilitate determining at least one of a dynamic strength of the sample, a dynamic modulus of the sample, and/or one or more additional dynamic properties of the sample as a function of the strain rate.

In a first example, a system of the present disclosure may include a first frame including a pair of guides and a mass movable along the pair of guides in a first (e.g., substantially vertical) direction. The system may also include one or more components configured to maintain the mass at a fixed location relative to the guides, and to controllably release the mass for movement in the first direction. In some embodiments, releasing the mass may cause the mass to impact one or more additional components of the system, thereby directly or indirectly imparting a dynamic force to a sample of material being tested.

Such an example system may also include a second frame having a second pair of guides, and a carrier movable along the second pair of guides in the first direction described above. In some examples, the second frame may be at least partly connected to the first frame while, in other examples, the second frame may be substantially separate from the first frame. Additionally, the second frame may include a modulator disposed on the carrier opposite the mass, and the modulator may be characterized by a particular respective strain rate. Thus, the dynamic force imparted to the sample of material by the carrier, or a component thereof, and resulting from an impact between the mass and the modulator, may be characterized by and/or may be a function of the particular strain rate of the modulator.

In some examples, the system may include one or more anvils movable with the carrier in response to an impact between the mass and the modulator. For example, at least one anvil may be connected to the carrier and may be positioned proximate, adjacent, and/or abutting a sample of material disposed beneath the carrier. In such examples, the impact between the mass and the modulator may drive the carrier and the anvil in the first direction, and may cause the anvil to impact the sample. Thus, the impact between the mass and the modulator may result in failure of the sample. In some embodiments, the sample may be disposed on a substantially horizontal base of either the first frame or the second frame. Alternatively, the sample may be supported above such a base by one or more additional anvils or other like support structures. Additionally, the sample may comprise a sheet of glass or other relatively brittle piece of material. In such examples, failure of the sample may comprise cracking, fracturing, shattering, or other breakage of the glass or other piece of material.

Such an example system may also include a plurality of sensors configured to determine various operating characteristics of the system and/or to determine various characteristics of the sample during testing. For example, the system may include a first sensor configured to detect a position and/or displacement of the carrier. In some examples, the first sensor may be configured to monitor the displacement and/or position of the carrier from the instant at which the mass contacts the modulator to a point in time at which failure of the sample occurs. In addition, the system may include a second sensor configured to determine a force applied to the modulator by the mass via the impact described above. In such examples, the second sensor may be configured to monitor the force applied to the modulator by the mass from the instant at which the mass contacts the modulator to a point in time at which failure of the sample occurs.

At least one of the sensors described herein may be operably and/or otherwise connected to a controller of the system, and such sensors may be configured to provide one or more signals to the controller indicative of the various characteristics being sensed, detected, monitored, and/or otherwise determined by the respective sensors. For example, the controller may be configured to receive input signals from the various sensors of the system, and to determine at least one of a dynamic strength of the sample and a dynamic modulus of the sample based on at least one of the inputs. As will be described below, the controller may determine a dynamic strength of the sample of material based on the determined force applied to the modulator as well as the strain rate of the modulator. Additionally and/or alternatively, the controller may determine a dynamic modulus of the sample of material based on the determined displacement of the carrier as well as the strain rate of the modulator.

In an additional embodiment, an example system of the present disclosure may include a first frame and a mass similar to those described above. Additionally, the system may include a test enclosure disposed opposite the mass and including a top wall, a base, and a number of sidewalls extending from the top wall to the base. Such a test enclosure may be configured to substantially surround the sample of material being tested. In some examples, the top wall, base, sidewalls, and/or other components of the test enclosure may define an internal space configured to retain any particles, gases, fluids, and/or other potentially harmful components or portions of the sample of material that may be jettisoned during the various testing procedures described herein.

In some examples, at least one of the components of the test enclosure may define a passage, and the system may further include a plunger movably disposed within the passage. For example, the plunger may have a first portion extending into the internal space and a second portion opposite the first portion extending substantially external to the test enclosure. In some examples, the plunger may include a replaceable tip that is positioned proximate, adjacent, and/or abutting a sample of material disposed within the internal space of the test enclosure.

The system may also include a modulator connected to the plunger opposite the mass. As described above, such a modulator may be characterized by a particular strain rate. Additionally, the modulator may be movable with the plunger in response to an impact between the mass and the modulator, and in some examples, the impact may cause failure of a casing of the sample of material. For example, the sample may comprise a rechargeable battery or other type of battery, and the battery may include an outer casing substantially enclosing one or more components thereof. As will be described in greater detail below, in such embodiments, failure of the casing may comprise piercing, puncture, or other breakage of the casing.

Such an example system may also include a first sensor configured to detect a displacement of the plunger corresponding to failure of the casing, and a second sensor configured to determine a force applied to the modulator by the mass and resulting in failure of the casing. Further, such a system may include a controller operably and/or otherwise connected to the various sensors described above. In such examples, the controller may be configured to determine at least one of a dynamic strength of the casing associated with the sample, as well as a dynamic modulus of the casing. As described above, in some embodiments the controller may determine such a dynamic strength based on, among other things, the force applied to the modulator by the mass, and the strain rate associated with the modulator. Additionally, the controller may determine such a dynamic modulus based on, among other things, the displacement of the plunger as well as the strain rate.

Since the various examples described herein provide ways to determine the dynamic strength, dynamic modulus, and/or other dynamic properties of various materials, embodiments of the present disclosure may assist in improving the reliability of electronic devices incorporating such materials and may, thus, increase user satisfaction. In particular, such methods enable users to determine various dynamic properties of substantially brittle device materials, substantially planar device materials, and/or device materials that may be combustible or otherwise dangerous when subjected to dynamic loads. Such capabilities solve a need that is not currently met by existing testing systems or dynamic testing methods.

Referring now to FIG. 1, a detailed example of a system 100 for determining one or more dynamic properties of a sample is illustrated. The example system 100 of FIG. 1 may include, among other things, a frame 102 configured to support one or more components of the system 100. For example, the frame 102 may comprise a first frame including a top support 104 and a base 106 disposed opposite the top support 104. The frame 102 may also include one or more guides extending from the top support 104 to the base 106. For example, the frame 102 may include a first guide 108 and a second guide 110 disposed opposite the first guide 108. In example embodiments, the first and second guides 108, 110 may extend substantially perpendicularly from the top support 104 and/or the base 106. The top support 104, the base 106, and/or one or more of the guides 108, 110 may be made from any substantially rigid material such as, for example, steel, aluminum, or other metals or alloys. Such materials may be configured to support one or more fixed and/or movable components of the system 100. For example, the base 106 may be configured to support the mass of various additional frames, sensors, modulators, and/or other components employed for the purpose of determining one or more dynamic parameters of a sample of material. The base 106 may be, for example, substantially planar and/or may include at least one substantially planar surface on which such components may be supported. In further examples, the base 106 may be omitted and, in such examples, the guides 108, 110 of the system 100 may be supported by a floor or other ground surface of the environment in which the system 100 is being used.

At least one of the guides 108, 110 may comprise substantially linear pillars, rods, rails, beams, and/or other structures extending in a substantially vertical direction relative to the base 106 and/or the top support 104. In some examples, the first guide 108 may extend substantially parallel to the second guide 110, and at least one of the guides 108, 110 may be configured to support various moving components of the system 100. In some examples, at least one of the guides 108, 110 may be configured to guide and/or otherwise direct movement of such movable components in a direction toward the base 106 and/or toward the top support 104. To facilitate guiding and/or otherwise directing movement of such movable components, at least one of the guides 108, 110 may include a substantially smooth, substantially rounded, substantially arcuate, and/or otherwise substantially circular surface with which such movable components may be slidably and/or otherwise movably engaged. For example, at least one of the guides 108, 110 may have a substantially circular cross-section and/or may be substantially cylindrical along a length thereof. In still further embodiments, at least one of the guides 108, 110 may include a substantially flat surface, substantially planar surface, a groove, a channel, and/or any other configuration configured to assist in guiding and/or otherwise directing movement of such movable components. In any of the examples described herein, such movable components and/or at least one of the guides 108, 110 may further include any combination of rollers, bearings, fittings, wheels, or other components configured to facilitate relative movement between such movable components and at least one of the guides 108, 110. It is understood that in further examples, the first frame 102 may include only a single guide 108, and in further examples, the first frame 102 may include more than two guides 108, 110.

The top support 104 may comprise one or more beams, plates, platforms, and/or other structures. In such examples, the top support 104 may have a configuration that is substantially similar to at least one of the guides 108, 110 and/or the base 106. The top support 104 may extend substantially parallel to the base 106, and may be connected to at least one of the guides 108, 110 in order to maintain the at least one of the guides 108, 110 in a fixed position relative to the various movable components of the system 100 during operation.

The system 100 may also include a mass 112, and the mass 112 may comprise a movable component of the system 100. For example, the mass 112 may be movable in a substantially linear direction along at least one of the guides 108, 110. The mass 112 may have any desired mass or weight, and in some examples, the mass 112 may have a mass of at least approximately 5 pounds. The mass 112 may be made from any material configured to withstand repeated impact with various other components of the system 100. For example, the mass 112 may comprise a substantially rigid bar, rod, plate, and/or other structure made from one or more of the materials described above respect to the components of the frame 102. In such examples, the mass 112 may be substantially non-brittle and substantially non-malleable. As a result, the mass 112 may be configured to withstand repeated impacts with additional components of the system 100 without failure and with negligible deformation.

The mass 112 may be connected to and/or slidably engaged with at least one of the guides 108, 110 such that the at least one of the guides 108, 110 may direct movement of the mass 112 relative to components of the frame 102. In some examples, the mass 112 may include any combination of rollers, bearings, fittings, wheels, or other components configured to facilitate movement of the mass 112 along a surface of at least one of the guides 108, 110. In some examples, the frame 102 may include one or more motors, solenoids, pneumatic components, and/or other mechanisms connected to the mass 112 and configured to move the mass 112 relative to, for example, at least one of the guides 108, 110. Additionally and/or alternatively, the mass 112 may be connected to and/or slidably engaged with at least one of the guides 108, 110 such that movement of the mass 112 relative to at least one of the guides 108, 110 may be induced substantially or solely by the force of gravity.

In some examples, the frame 102 may also include one or more components configured to selectively induce movement of the mass 112. For example, the frame 102 may include at least one lock selectively engaged with the mass 112 and configured to fix the mass 112 at a desired location along, for example, at least one of the guides 108, 110 and/or relative to the top support 104. In some examples, the at least one lock may be supported by and/or connected to at least one of the guides 108, 110 and/or to the top support 104. The lock may comprise, for example, an electromagnet or other selectively energizeable component configured to fix the mass 112 relative to at least one of the guides 108, 110 in a first (e.g., activated) state, and to release the mass 112 for movement relative to at least one of the guides 108, 110 in a second (e.g., deactivated) state. In such examples, the lock may be configured to generate an electromagnetic field attracting the mass 112 in the first state, and may be configured to discontinue generation of such an electromagnetic field in the second state. By discontinuing such an electromagnetic field, the mass 112 may be free to move, due to the force of gravity acting on the mass 112, in the direction of arrow 118 away from the top support 104 and towards the base 106.

In further examples, the lock may comprise one or more latches, pins, hooks, arms, shoulders, or other substantially mechanical components movable relative to the mass 112 or a component thereof. In such examples, the lock may further comprise one or more solenoids, motors, pneumatic components, piezoelectric components, or other components configured to actuate at least one of the mechanical components described above. Such components may be configured to engage at least a portion of the mass 112 in order to fix the mass 112 relative to at least one of the guides 108, 110 in a first position. Further, actuation of one or more such components may enable the mass 112 to move, due to the force of gravity, in the direction of arrow 118.

In still further examples, the frame 102 may include a first lock 114 and a second lock 116 disposed opposite the first lock 114. Although the first and second locks 114, 116 are illustrated schematically in FIG. 1 as being connected to the first and second guides 108, 110, respectively, in further examples, at least one of the first and second locks 114, 116 may be connected to the top support 104 and/or to one or more additional stationary components of the frame 102.

In some embodiments, the system 100 may also include a second frame 120. In such embodiments, one or more components of the second frame 120 may be substantially similar in shape, size, weight, and/or other aspects to a corresponding component of the first frame 102. Additionally, one or more components of the second frame 120 may be supported by the base 106, at least one of the guides 108, 110, the top support 104, and/or other components of the first frame 102. For example, the second frame 120 may include at least one guide, and in some examples, the at least one guide may be connected to, supported by, and/or otherwise engaged with the base 106. As shown in FIG. 1, in some examples the second frame 120 may include a first guide 122 and a second guide 124 disposed opposite the first guide 122.

Similar to the guides 108, 110 described above, the guides 122, 124 may comprise substantially linear pillars, rods, rails, beams, and/or other structures extending in a substantially vertical direction relative to the base 106 and/or the top support 104. In some examples, the first guide 122 may extend substantially parallel to the second guide 124, and at least one of the guides 122, 124 may extend substantially parallel to at least one of the guides 108, 110. Further, at least one of the guides 122, 124 may be configured to support various moving components of the second frame 120. In some examples, at least one of the guides 122, 124 may be configured to guide and/or otherwise direct movement of such movable components of the second frame 120 toward the base 106 and/or toward the top support 104. To facilitate guiding and/or otherwise directing movement of such movable components, at least one of the guides 122, 124 may include a substantially smooth, substantially rounded, substantially arcuate, and/or otherwise substantially circular surface with which such movable components may be slidably and/or otherwise movably engaged. For example, at least one of the guides 122, 124 may have a substantially circular cross-section and/or may be substantially cylindrical along a length thereof. In still further embodiments, at least one of the guides 122, 124 may include a substantially flat surface, a substantially planar surface, a groove, a channel, and/or any other configuration configured to assist in guiding and/or otherwise directing movement of such movable components. In any of the examples described herein, such movable components and/or at least one of the guides 122, 124 may further include any combination of rollers, bearings, fittings, wheels, or other components configured to facilitate relative movement between such movable components and at least one of the guides 122, 124. It is understood that in further examples, the second frame 120 may include only a single guide 122, and in further examples, the second frame 120 may include more than two guides 122, 124.

Additionally, at least one of the guides 122, 124 may be configured to withstand an impact from the mass 112 and/or support one or more components of the second frame 120 impacted by the mass 112 as the mass 112 travels in the direction of arrow 118. For example, in some embodiments the second frame 120 may include one or more components disposed and/or otherwise configured to impede movement of the mass 112 in the direction of arrow 118 such as, for example, when the mass 112 is released from the position illustrated in FIG. 1. In such examples, the second frame 120 and its components may be configured to withstand such impact with negligible deformation and substantially without failure. In some examples, such impacts may be useful in determining one or more dynamic properties of a sample of material disposed within, supported by, and/or otherwise associated with the second frame 120. For example, as will be described in greater detail below, in some embodiments a force imparted by the mass 112 via such impacts may be measured and/or otherwise determined. In such embodiments, the determined force may be utilized as an input to one or more algorithms, lookup tables, neural networks, and/or other components of the system 100 for determining a dynamic yield strength, a dynamic Young's modulus, and/or other dynamic property of a sample of material.

In some examples, the second frame 120 may also include a carrier 126. In such examples, the carrier 126 may be connected to, supported by, movable relative to and/or otherwise associated with at least one of the guides 122, 124. The carrier 126 may be connected to and/or slidably engaged with at least one of the guides 122, 124 such that the at least one of the guides 122, 124 may direct movement of the carrier 126 relative to components of the frame 102. For example, the carrier 126 may be movable in a substantially linear direction along at least one of the guides 122, 124. In some examples, the carrier 126 may include any combination of rollers, bearings, fittings, wheels, or other components configured to facilitate movement of the carrier 126 along a surface of at least one of the guides 122, 124 and in the direction of arrow 118.

The carrier 126 may be made from any material configured to withstand repeated impact with various other components of the system 100, such as the mass 112. For example, the carrier 126 may comprise a substantially rigid bar, rod, plate, and/or other structure made from one or more of the materials described above respect to the components of the frame 102. In such examples, the carrier 126 may be substantially non-brittle and substantially non-malleable. As a result, the carrier 126 may be configured to support one or more components of the system 100 subjected to repeated impacts by the mass 112 without failure and with negligible deformation. For example, the carrier 126 may support and/or otherwise carry a modulator 128 as well as a sensor 130 configured to measure, sense, and/or otherwise determine various characteristics of the modulator 128 and/or the carrier 126 during operation of the system 100. The modulator 128 may comprise one or more pieces and/or samples of material having known physical characteristics. For example, the modulator 128 may be selected based on a known strain rate (s/sec), durometer, mass, tensile strength, yield strength ($\sigma$) Young's modulus (M), and/or other properties thereof. The modulator 128 may be made from any of the materials described above with respect to the components of the frame 102. Alternatively, the modulator 128 may be made from rubber, plastic, wood, ceramics, and/or any other polymer, synthetic material, or non-synthetic material. In some examples the modulator 128 may comprise a shock absorber, a spring, a damper, a gasket, and/or any other like structure configured to withstand multiple impacts from the mass 122.

In some examples, causing a first impact between the mass 112 and a first modulator 128(1) may result in, for example, a first force being applied to a first sample of material disposed within the second frame 120 and/or beneath the carrier 126, and causing a second impact between the mass 112 and a second modulator 128(2) different from the first modulator 128(1) may result in a second force being applied to the first sample or to a different second sample. In such examples, the first force may be different from the second force. For instance, a relatively rigid first modulator 128(1) may be characterized by relatively high strain rate and may, thus, be configured to transmit a relatively high force to the carrier 126 when the first modulator 128(1) is impacted by the mass 112. Conversely, a relatively malleable second modulator 128(2) may be characterized by a relatively low strain rate and may, thus, be configured to transmit a relatively lower force to the carrier 126 when impacted by the mass 112.

In some examples, strain rate and/or other known parameters of the modulator 128 may be utilized as inputs to one or more algorithms, lookup tables, neural networks, and/or other components of the system 100 for determining a dynamic yield strength, a dynamic Young's modulus, and/or other dynamic property of a sample of material that is, for example, impacted by one or more structures associated with the carrier 126. In such examples, the sensor 130 may comprise one or more force sensors configured to determine a force imparted to the modulator 128 by the mass 112 as the mass 112 impacts the modulator 128. In some examples, the sensor 130 may be disposed adjacent to the modulator 128 in order to determine such force. In further examples, the sensor 130 may be disposed substantially between the modulator 128 and the carrier 126. For example, a bottom surface A of the mass 112 may be separated from a top surface B of the modulator 128 by a distance H, and the force sensor 130 may be disposed on a top surface C of the carrier 126 at a location between the modulator 128 and the carrier 126. In example embodiments, the sensor 130 may comprise a flexible printed circuit, a force sensing resistor, a load cell, a piezoelectric force sensor, a force transducer, a pressure sensor, and/or any other type of sensor configured to determine a force imparted directly to the sensor 130 and/or to an item to which the sensor 130 is connected. In such examples, a force imparted to the modulator 128 as a result of an impact between the mass 112 and the modulator 128 may be determined by the force sensor 130, and the force sensor 130 may generate an output indicative of such a determined force.

Further, in example embodiments such an impact between the mass 112 and the modulator 128 may cause the carrier 126 to move in the direction of arrow 118. In such examples, the carrier 126 and/or a component connected to the carrier 126 may contact and/or impact a sample S of material. In such embodiments, the force determined by the force sensor 130 may approximate and/or may be substantially equal to the force imparted to the sample S by the carrier 126 and/or by the component of the carrier 126. The sample S may comprise any of the materials described herein with respect to components of the first frame 102 and/or with respect to the modulator 128. For example, the sample S may comprise steel, aluminum, a metal, an alloy, a ceramic, a polymer, and/or any other material. In further embodiments, the sample S may comprise glass, and may be formed into a substantially planar piece or sheet. The sample S may have any desirable weight, length, width W, thickness T, or other configuration.

In further examples, the sample S may comprise one or more devices, mechanical components, electrical components, or other structures. For example, the sample S may comprise a printed circuit board, a display of an electronic device, a battery of an electronic device, an outer housing of an electronic device, or other components. In some examples, the sample S may include an outer casing or other structure configured to house such components. For example, in embodiments in which the sample S comprises a battery sample, the sample S may include an outer casing made of one or more polymers, alloys, and/or any of the other materials described herein. Such an outer casing may substantially surround and/or otherwise enclose, for example, various battery cells and/or other battery components. Such battery samples S may comprise, for example, sealed dry cell batteries such as nickel cadmium, nickel zinc, nickel metal hydride, lithium-ion, nanoball, low self-discharging and/or other batteries.

In some examples, the system 100 may also include one or more components configured to selectively permit movement of the carrier 126 and/or components thereof. For example, the frame 120 may include at least one lock selectively engaged with the carrier 126 and configured to fix the carrier 126 at a desired location along, for example, at least one of the guides 122, 124 and/or relative to the mass 112. In some examples, the at least one lock may be supported by and/or connected to at least one of the guides 122, 124 of the second frame 120, and/or to one of the guides 108, 110 of the first frame 102. The lock may comprise, for example, an electromagnet or other selectively energizable component configured to fix the carrier 126 relative to at least one of the guides 122, 124 in a first (e.g., activated) state, and to release the carrier 126 for movement relative to at least one of the guides 122, 124 in a second (e.g., deactivated) state. In such examples, the lock may be configured to generate an electromagnetic field attracting the carrier 126 in the first state, and may be configured to discontinue generation of such an electromagnetic field in the second state. Thus, when activated, the lock may apply a magnetic counterforce to the carrier 126 in a direction opposite the direction of arrow 118. In some examples, the counterforce applied to the carrier 126 by the lock may be greater than or substantially equal to a total weight of the carrier 126, the modulator 128, and any other components of the system 100 carried by the carrier 126. By discontinuing such an electromagnetic field, and thus discontinuing the application of such a counterforce, the carrier 126 may be free to move, due to the force of gravity acting on the carrier 126, in the direction of arrow 118 away from the top support 104 and towards the base 106.

In further examples, the lock may comprise one or more latches, pins, hooks, arms, shoulders, or other substantially mechanical components movable relative to the carrier 126 or a component thereof. In such examples, the lock may further comprise one or more solenoids, motors, pneumatic components, piezoelectric components, or other components configured to actuate such mechanical components. Such components may be configured to fix the carrier 126 relative to at least one of the guides 122, 124 in a first position, and actuation of one or more such components may enable the carrier 126 to move, due to the force of gravity, in the direction of arrow 118.

In still further examples, the frame 120 may include a first lock 132 and a second lock 134 disposed opposite the first lock 132. Although the first and second locks 132, 134 are illustrated schematically in FIG. 1 as being connected to the first and second guides 122, 124, respectively, in further examples, at least one of the first and second locks 132, 134 may be connected to a corresponding one of the guides 108, 110 and/or to one or more additional stationary components of at least one of the frames 102, 120.

In example embodiments, the system 100 may also include an additional sensor 136 configured to determine one or more operational characteristics of the carrier 126, the modulator, or other components associated with the second frame 120. For example, the sensor 136 may comprise one or more position sensors configured to sense, measure, and/or otherwise determine displacement and/or movement of the carrier 126, the modulator 128, and/or one or more other components associated with the second frame 120. Such sensors 136 may comprise, for example, linear variable differential transformer (LVDT) sensors, laser sensors, capacitive displacement sensors, ultrasonic sensors, inductive noncontact position sensors, multi-access displacement transducers, and/or any other absolute or relative position sensors. Such position sensors 136 may include linear, angular, or multi-axis sensors.

In some examples, the position sensor 136 may be fixed relative to the carrier 126, the modulator 128 and/or other components associated with the second frame 120 in order to determine displacement and/or movement thereof. For example, the position sensor 136 may be fixedly connected to one of the guides 108, 110 of the first frame 102 and may be positioned to determine movement of the carrier 126 relative thereto. Alternatively, at least a portion of the position sensor 136 may be fixedly connected to the carrier 126, the modulator 128, and/or other components associated with the second frame 120. In such embodiments, the portion of the position sensor 136 may be movable with one or more movable components of the system 100, and may be configured to determine movement thereof relative to one or more fixed components of the system 100. In the examples described herein, the position sensor 136 may generate an output indicative of such a determined displacement and/or movement. The determined displacement and/or movement may be utilized as an input to one or more algorithms, lookup tables, neural networks, and/or other components of the system 100 for determining a dynamic yield strength, a dynamic Young's modulus, and/or other dynamic properties of the sample S of material.

As shown in FIG. 1, the system 100 may also include a mechanism 138 configured to selectively apply a counterforce to the mass 112. For example, the mechanism 138 may be positioned and/or otherwise configured to prevent multiple impacts between the mass 112 and the modulator 128. For example, once a first impact has occurred between the mass 112 and the modulator 128, it may be desirable to prevent the mass 112 from repeatedly striking, bouncing off, impacting, and/or otherwise contacting the modulator 128. Accordingly, in some embodiments the system 100 may also include an additional sensor 140 configured to determine the location and/or position of the mass 112. In such examples, the sensor 140 may comprise a position sensor substantially similar to, for example, the sensor 136 described above. The sensor 140 may be configured to determine a position of the mass 112 corresponding to a first impact between the mass 112 and the modulator 128. For example, the sensor 140 may be positioned and/or otherwise configured to determine a location of the mass 112 corresponding to contact between the bottom surface A of the mass 112 and the surface B of the modulator 128. Additionally and/or alternatively, the sensor 140 may be positioned and/or otherwise configured to determine a location of the mass 112 corresponding to imminent contact between the surfaces A, B. The sensor 140 may be configured to generate an output indicative of such a position, and the mechanism 138 may be activated in response to such an output. Alternatively, and/or additionally, the force sensor 130 may be configured to generate an output indicative of contact between the mass 112 and the modulator 128, and the mechanism 138 may be activated and/or may apply a counterforce to the mass 112 in the direction of arrow 142 in response to such an output from the sensor 130. In such examples, the counterforce applied by the mechanism 138 may be greater than or substantially equal to the weight of the mass 112.

The mechanism 138 may comprise, among other things, one or more solenoids, motors, compression springs, weights, electromagnets, pneumatic actuators, piezoelectric actuators, and/or other components configured to selectively apply a force and/or counterforce to a movable component of the system 100. For example, the mechanism 138 may comprise a pull the solenoid including shaft or other component connected to the mass 112, and a housing or other component connected to the top support 104 and/or another stationary component of the system 100. The mechanism 138 may be controlled to apply the counterforce described above to the mass 112 in response to one or more signals received from the sensor 140.

In some examples, the system 100 may also include one or more controllers 144 configured to control operation of at least one of the first and second locks 114, 116, the first and second locks 132, 134, and/or the mechanism 138. For example, each of the sensors 130, 136, 140 may be operably connected to and/or otherwise in communication with the controller 144. For example, the various signals generated by one or more of the sensors 130, 136, 140 may be directed to the controller 144 and/or various components thereof for processing. In some examples, the controller 144 may be configured to use information contained in one or more such signals as an input into one or more algorithms, lookup tables, neural networks and/or other components of the controller 114. In such embodiments, the controller 144 may determine at least one of a dynamic strength of the sample S and a dynamic modulus of the sample S based on one or more such inputs. For example, the dynamic strength of the sample S may be based on the force applied to the modulator 128 by the mass 112 at impact as well as a strain rate associated with the modulator 128. In additional examples, the dynamic modulus may be based on the force applied to the modulator 128 by the mass 112 at impact, as well as the strain rate associated with the modulator 128, and/or a determined displacement of the carrier 126. In example embodiments, the controller 144 may comprise one or more processors, memory, and/or other components configured to assist in determining such dynamic parameters of the sample S.

With continued reference to FIG. 1, in some examples the sample S may be supported by and/or otherwise disposed on one or more support structures located on the base 106. For example, the system 100 may include at least one anvil 146 disposed beneath the sample S. In some examples, the sample S may be disposed on a single anvil 146(1), and in other examples, the sample S may be disposed on two or more anvils 146(1), 146(2). In addition, at least one anvil 146(3) may be carried by and/or otherwise connected to the carrier 126. For example, at least one anvil 146(3) may be disposed on and/or otherwise connected to a bottom surface D of the carrier 126. The carrier 126 and/or the anvil 146(3) may be positioned such that a peak of the anvil 146(3) is disposed adjacent to and/or abuts against a top surface E of the sample S when the carrier 126 is in the stationary and/or locked position shown in FIG. 1. In such examples, a bottom surface F of the sample S may be supported by the anvils 146(1), 146(2), and the anvils 146(1), 146(2) may be spaced by a distance L. In such examples, the distance L may be less than or substantially equal to the width W of the sample S, and the distance L may be measured between, for example, a respective peaks of the anvils 146(1), 146(2). In such examples, the distance L may be utilized as an additional input in one or more algorithms, lookup tables, neural networks, and/or other components of the system 100 used to determine one or more dynamic parameters of the sample S.

In example embodiments, at least one of the anvils 146 described herein may be made from any of the materials described above with respect to, for example, the frame 102 and/or the modulator 128. For example, at least one of the anvils 146 may be made from a metal, alloy, or other material configured to support the sample S. Additionally, the anvils 146 may be shaped, sized, and/or otherwise configured to facilitate failure of the sample S in response to impact between the mass 112 and the modulator 128. For example, at least one of the anvils 146 may include a substantially angled, substantially pointed peak configured to bend, penetrate, break, crack, fracture, shatter, and/or otherwise cause failure of the sample S as the carrier 146 is moved in the direction of arrow 118 due to the impact between the mass 112 and the modulator 128.

In further examples, various anvil configurations may be used for testing of the sample S. For instance, although FIG. 1 illustrates an embodiment in which three anvils 146 may be employed for a three-point bending test, in further examples, two anvils 146 may be employed for a two-point bending test of the sample S. In additional examples, four anvils 146 may be employed for a four-point bending test. In still further examples, the anvils 146 may be replaced with other support and/or impact structures for such testing. For example, in embodiments in which a ball-on-ring bending test is performed using the system 100, the anvil 146(3) may be replaced with a substantially rounded or substantially spherical ball-like structure for impacting the top surface E of the sample S. Additionally, the anvils 146(1), 146(2) may be replaced with a substantially hollow, substantially cylindrical ring-like support structure for supporting the bottom surface F of the sample S. Alternatively, in embodiments in which a ring-on-ring bending test is performed using the system 100, the anvils 146(1), 146(2) may be replaced with a first substantially hollow, substantially cylindrical ring-like support structure for supporting the bottom surface F of the sample S. This first support structure may have a corresponding first inner diameter and a first outer diameter. Additionally, the anvil 146(3) may be replaced with a second substantially hollow, substantially cylindrical ring-like structure for impacting the top surface E of the sample S. The second structure may have a second inner diameter and a second outer diameter, and the second outer diameter of the second structure may be different from the first inner diameter of the first structure. For example, the second outer diameter of the second structure impacting the top surface E may be smaller than the first inner diameter of the first support structure supporting the bottom surface F of the sample S.

In some embodiments, the system 100 may be utilized to determine various dynamic parameters of any of the samples S described above. In some examples, however, it may be desirable to dispose one or more such samples S within an enclosure in order to perform various procedures utilized in determining such parameters. For example, puncturing or other failure of one or more of the samples S described herein may cause the sample S to emit dangerous and/or harmful gases, particles, and/or other components. Additionally or alternatively, breakage or other failure of one or more of the samples S, such as a sample S made from glass or other relatively brittle materials, may cause shards of the material to project in various directions upon being impacted by, for example, at least one of the anvils 146(3). Accordingly, in such embodiments disposing such a relatively brittle sample S within an enclosure may reduce the risk of harm or injury to a user.

Figure 2:
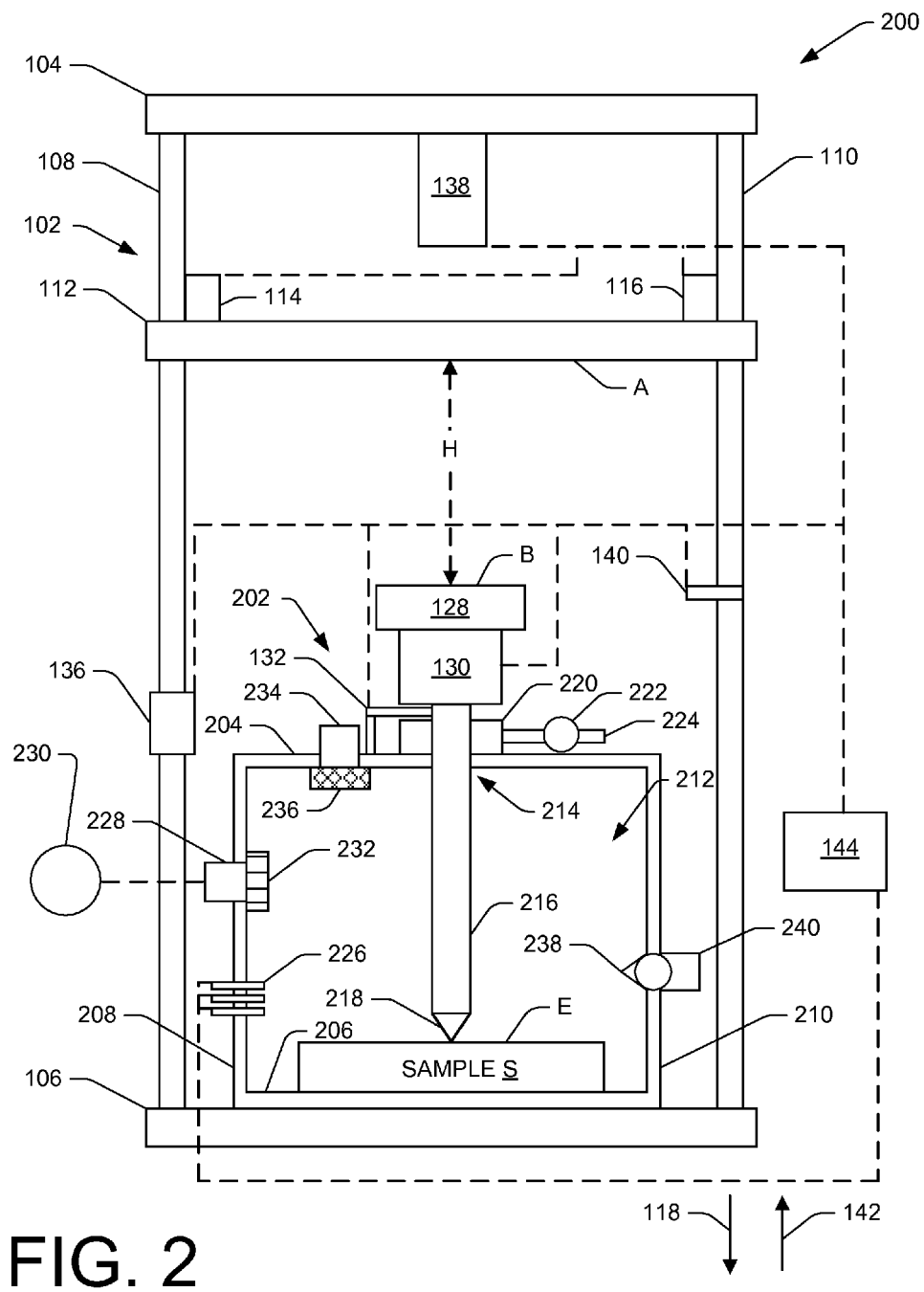
FIG. 2 illustrates another example system for determining one or more dynamic properties of a sample.

FIG. 2 illustrates another example system 200 of the present disclosure including a test enclosure 202 configured to contain such relatively brittle and/or relatively dangerous samples S during operation. Whenever possible, like item numbers have been used in FIGS. 1 and 2 to identify substantially similar and/or identical components of the respective systems 100, 200. In example embodiments, the test enclosure 202 may comprise a substantially box-like structure including a top wall 204, a base 206 opposite the top wall 204, and a plurality of side walls 208, 210 extending from the top wall 204 to the base 206. In the example embodiment of FIG. 2, only a pair of side walls 208, 210 are shown for clarity, but it is understood that at least one or two additional sidewalls may be included in the test enclosure 202 in order to form a substantially enclosed internal space 212 within the test enclosure 202.

In some examples, the test enclosure 202 may include at least one door (not shown), window, or other like component that may be opened in order to insert and/or remove the sample S from the internal space 212. Such a component may be, for example, hingedly attached to one or more of the sidewalls 208, 210. The top wall 204, base 206, sidewalls 208, 210, and/or other components of the test enclosure 202 may be made from any of the materials described above with respect to, for example, the frame 102 and/or the modulator 128. For example, the test enclosure 202 may be made from steel, aluminum, and/or any other substantially rigid material in order to contain particles, gases, and/or other components of the sample S that may be projected in various directions as the sample S is impacted by one or more components of the system 200.

In some examples, the top wall 204, the sidewalls 208, 210, and/or other components of the test enclosure 202 may include one or more openings or other such passages 214. Such passages 214 may allow additional components of the system 200 to be mechanically connected to the test enclosure 202 and/or fluidly connected to the internal space 212. Additionally, such passages 214 may, in some examples, permit relative movement between one or more components of the system 200 and the test enclosure 202. For example, the system 200 may include one or more plungers 216 extending from within the internal space 212 to a location external to the test enclosure 202. One or more such plungers 216 may include a removable tip 218, and maybe movable relative to the test enclosure 202 in the direction of arrow 118 toward the sample S and in the direction of arrow 142 away from the sample S.

In example embodiments, one or more of the plungers 216 described herein may be substantially similar to at least one of the anvils 146 described above. For example, a plunger 216 and the tip 218 of the present disclosure may be made of any of the materials described above with respect to the first frame 102 and/or the modulator 128. In some examples, the tip 218 may be shaped, sized, and/or otherwise configured to facilitate failure of the sample S in response to impact between the mass 112 and the modulator 128. For example, the tip 218 may include a substantially angled, substantially pointed peak configured to bend, indent, penetrate, puncture, pierce, and/or otherwise break the sample S as the plunger 216 is moved in the direction of arrow 118 due to an impact between the mass 112 and the modulator 128.

Additionally, an example plunger 216 may be substantially rectangular, substantially cylindrical, and/or any other shape in order to facilitate movement of at least a portion of the plunger 216 into and/or out of the internal space 212 via the passage 214. For example, at least a portion of the plunger 216 may have an outer diameter that is substantially equal to and/or that is incrementally smaller than a diameter of the passage 214. Such a configuration may facilitate a sliding engagement between, for example, the outer diameter of the plunger 216 and the passage 214. In some embodiments, the test enclosure 202 may further include any combination of rollers, bearings, fittings, wheels, or other components configured to facilitate relative movement between the plunger 216 and the passage 214.

As shown in FIG. 2, in some examples the test enclosure 202 may include a vacuum chamber 220 substantially surrounding a portion of the plunger 216 disposed external to the test enclosure 202. In such examples, the vacuum chamber 220 may be fluidly connected to the internal space 212 via the passage 214. The test enclosure 202 may also include a vacuum pump 222 fluidly connected to the vacuum chamber 220 and configured to direct a negative pressure to the internal space 212 via the passage 214. For example, the vacuum pump 222 may be configured to direct a negative pressure to the vacuum chamber 220, and such a negative pressure may be applied to the internal space 212 of the test enclosure 202 by way of the vacuum chamber 220. In example embodiments, the negative pressure applied to the internal space 212 by the vacuum pump 222 may assist in removing any fumes, leaks, and/or other fluids released from the sample S during use of the system 200. Such fluids may, for example, pass to one or more filters and/or an exhaust system associated with the system 200 via an output 224 of the vacuum pump 222 and/or the vacuum chamber 220. In example embodiments, the vacuum pump 222 may apply a vacuum to the internal space 212 such that a fluid pressure within the internal space 222 is less than an atmospheric pressure external to the test enclosure 202.

The test enclosure 202 may also include a variety of additional components configured to assist in determining one or more dynamic parameters of the sample S. For example, the system 200 may include one or more additional sensors 226 connected to the sample S. For example in embodiments in which the sample S comprises a battery sample, such sensors 226 may be connected to the battery sample S and configured to determine at least one operating characteristic of the battery sample S as the plunger 216 impacts the battery sample S. For example, such sensors 226 may be configured to determine whether or not sample S is fully operable. Additionally, such sensors 226 may be configured to determine failure of such a battery sample. In example embodiments, such failure may be determined by, for example, a signal from one or more of the sensors 226 indicating that a casing of the battery sample S has been pierced, punctured, and/or otherwise breached. Alternatively, such failure may be determined by a signal from one or more of the sensors 226 indicating that the battery sample S is no longer capable of storing an electrical charge and/or discharging electrical power stored therein. Accordingly, in some embodiments at least one of the sensors 226 may comprise a diagnostic sensor configured to sense, monitor, detect, and/or otherwise determine functionality of the battery sample S. In still further embodiments, the sensors 226 may comprise at least one of a temperature sensor or a voltage sensor. For example, the sensors 226 may include a thermocouple, thermopile, or other temperature sensor configured to determine a steady state temperature of the battery sample S and/or an increase in temperature caused by a short circuit of the battery sample S related to failure of the outer casing. The sensors 226 may also include a voltage sensor configured to determine a steady state voltage of the battery sample S and/or a decrease in voltage caused by a short circuit of the battery sample S related to failure of the outer casing.

The test enclosure 202 may also include one or more inlets 228 fluidly connected to a pressurized fluid supply 230. For example, the pressurized fluid supply 230 may include a supply of pressurized nitrogen, and/or other nonflammable fluids. In such examples, such nonflammable fluids may be selectively supplied to the internal space 212 via the inlet 228 as a means of suppressing and/or substantially prohibiting combustion within the internal space 212 caused by impact between the plunger 216 and the sample S. The test enclosure 202 may also include one or more flame arrestors 232 fluidly connected to the inlet 228 to further assist in preventing combustion caused by impact between the plunger 216 and the sample S. In some examples, the flame arrestor 232 may comprise one or more filters, valves, and/or other like devices configured to restrict fluid disposed within the internal space 212 from exiting the internal space 212 via the inlet 228. For example, the flame arrestor 232 may comprise one or more check valves configured to prevent the back flow of nitrogen to the pressurized fluid supply 230. Such a check valve may also be configured to prevent a flame originating within the internal space 212 from traveling to the pressurized fluid supply 230 via the inlet 228.

The test enclosure 202 may further include an additional outlet 234 and at least one of a filter or a muffler 236 connected to the outlet 234. In such examples, the least one of the filter or the muffler 236 may be configured to capture particles or other components of a flow of fluid exiting the internal space 212 via the outlet 234. Such particles and/or other components of the flow of fluid may be expelled from the sample S as a result of the impact between the plunger 216 and the sample S. Additionally, such a muffler 236 may dampen sound and/or vibration caused by the impact between the plunger 216 and the sample S.

In additional examples, the test enclosure 202 may include at least one pressure relief valve 238 configured to prevent sudden buildups of fluid pressure within the internal space 212. For example, such a relief valve 238 may comprise a check valve fluidly connected to an outlet 240 of the test enclosure 202. In example embodiments, the relief valve 238 may be configured to maintain a fluid pressure within the internal space 212 of the test enclosure 202 at a level less than or substantially equal to a threshold pressure. In example embodiments, such a threshold pressure may correspond to a pressure at which a substantially fluid tight seal formed by the relief valve 238 may open, thereby releasing fluid disposed within the internal space 212 via the outlet 240. Some examples, the threshold pressure associated with the relief valve 238 may be greater than or substantially equal to 10 PSI. In further example embodiments, such an example threshold pressure may be greater than or substantially to 5 PSI. In still further examples, the threshold pressure may be greater than or substantially equal to 1 PSI. It is understood that, as used herein, the term "fluid" may include liquids or gases.

As shown in FIG. 2, in the example system 200 the carrier 126 described above with respect to the system 100 may be omitted. Accordingly, during use the tip 218 of the plunger 216 may be positioned proximate the top surface E of the sample S, and the mass 112 may be released to cause an impact between the mass 112 and the modulator 128 connected to the plunger 216 external to the test enclosure 202. Such impact may move the plunger 216 in the direction of arrow 118, and may result in failure of the sample S. For example, the sample S may comprise a battery sample including an outer casing. In such examples, impact between the mass 112 and the modulator 128 may move the plunger 216 in the direction of arrow 118 to bend, indent, breach, pierce, puncture, break, and/or otherwise cause failure of the casing associated with the battery sample S.

Additionally, the sensor 136 may measure, calculate, and/or otherwise determine a displacement of the plunger 216 caused by the impact described above, and the force sensor 130 may determine the force applied to the modulator 128 by the mass 112 during such an impact. The controller 144 may then determine at least one of a dynamic strength of the casing of the battery sample S and a dynamic modulus of the casing based on such determined variables.

Figure 3:
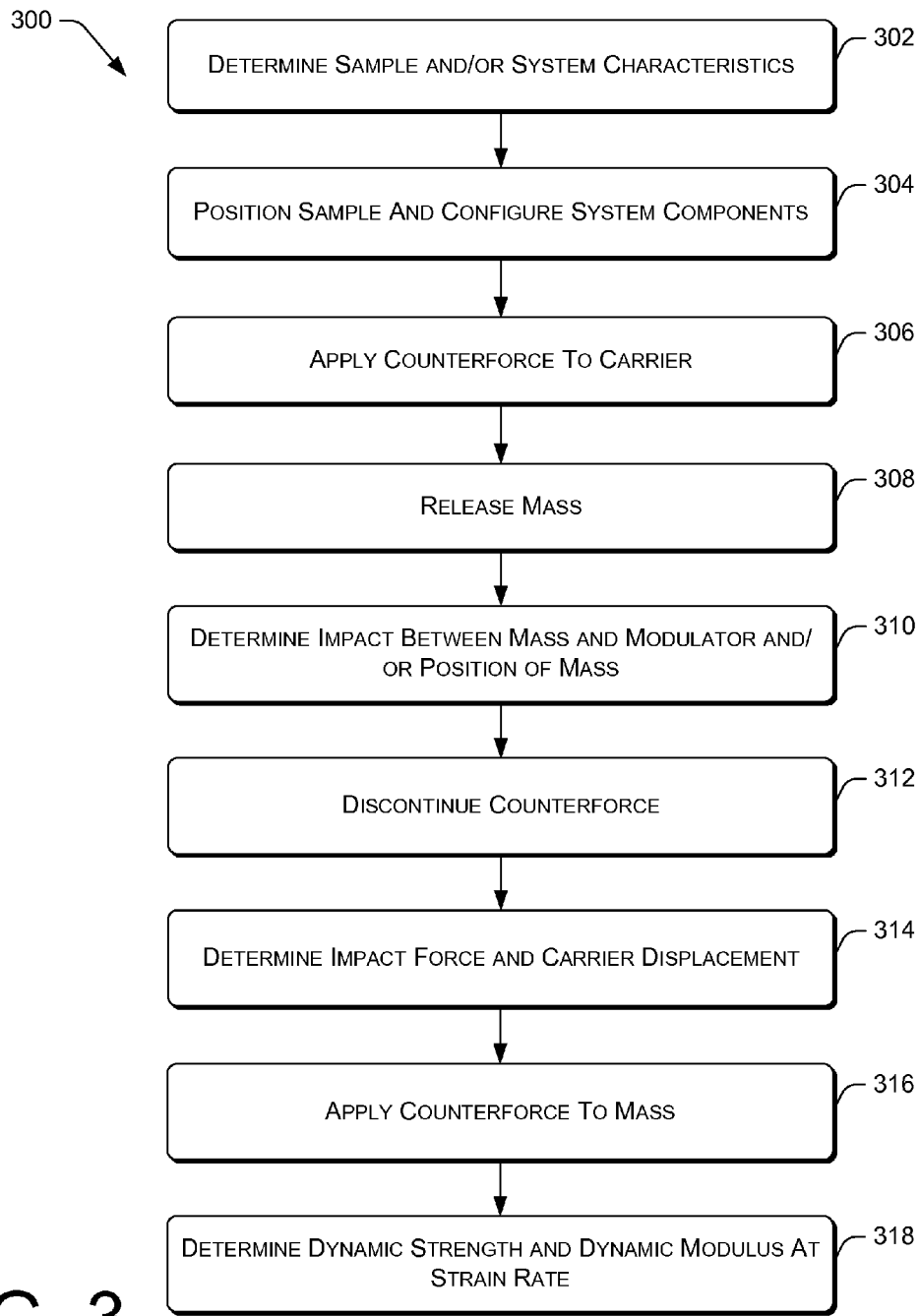
FIG. 3 illustrates a flow diagram of an example method for determining one or more dynamic properties of a sample.

FIG. 3 illustrates a flow diagram of an example method 300 of determining one or more dynamic properties and/or parameters of a sample of material. In some instances, the method 300, or portions thereof, may be repeated one or more times in order to assist in determining such dynamic parameters. The example method 300 is illustrated as a collection of blocks in a logical flow diagram, which represent a sequence of operations, some or all of which can be implemented in hardware, software or a combination thereof. In the context of software, the blocks represent computer-executable instructions stored on one or more computer-readable media of the controller 144 that, when executed by one or more processors of the controller 144, perform the recited operations. Generally, computer-executable instructions include routines, programs, objects, components, data structures and the like that perform particular functions or implement particular abstract data types. The order in which the operations are described should not be construed as a limitation. Any number of the described blocks can be combined in any order and/or in parallel to implement the process, or alternative processes, and not all of the blocks need be executed. For discussion purposes, the methods herein are described with reference to the systems 100, 200, frameworks, architectures, and environments described in the examples herein, although the methods may be implemented in a wide variety of other systems, frameworks, architectures, or environments.

The description of the various methods may include certain transitional language and directional language, such as "then," "next," "thereafter," "subsequently," "returning to," "continuing to," "proceeding to," etc. These words, and other similar words, are simply intended to guide the reader through the graphical illustrations of the methods and are not intended to limit the order in which the method steps depicted in the illustrations may be performed.

Beginning at 302, the method 300 includes determining at least one sample and/or system characteristic. For example, as part of determining a dynamic strength of the sample S, a dynamic modulus of the sample S, and/or other like dynamic property of a material included in the sample S, a user of the system 100 may calculate, measure, and/or otherwise determine at least one of the width W, thickness T, length, weight, composition, durometer, and/or other characteristics of the sample S. At 302, the user may also determine the weight of the mass 112, the composition and/or strain rate (s/sec) of the modulator 128, and/or other system characteristics. As noted above, the sample S may comprise any of a variety of materials, devices, batteries, or other objects. For purposes of the method 300 described herein, and for ease of description, a sample S comprising a substantially planar sheet of glass, such as glass utilized as a component of a touch screen or other electronic device display will be described unless otherwise noted.

At 304, the user may position the sample S at a desired location relative to one or more components of the system 100 and may configure various components of the system 100 to assist in determining one or more of the dynamic properties described above. For example, the user may position the sample S on at least one anvil 146 such that a bottom surface F of the sample S is at least partly supported by the anvil 146. In some examples, the sample S may be disposed in a substantially horizontal orientation on at least one anvil 146(1). Such an example horizontal orientation of the sample S is illustrated in FIG. 1. In alternative examples, the sample S may be disposed in a substantially vertical orientation (e.g., substantially perpendicular to the orientation illustrated in FIG. 1) on at least one anvil 146(1). Additionally, at 304, a second and/or at least one additional anvil 146(3) may be positioned proximate, adjacent to, and/or abutting a top surface E of the sample S. In such examples, the second and/or at least one additional anvil 146(3) may be connected to and/or otherwise supported by the carrier 126, and may be movable with the carrier 126 in the direction of arrow 118 toward the sample S and/or the at least one anvil 146(1).

At 304, the user may also activate and/or energize one or more of the sensors described above. For example, the force sensor 130, the position sensor 136, and/or the position sensor 140 may be activated at 304 in order to measure, calculate, sense, and/or otherwise determine the various operating characteristics of the system 100 described above with respect to such sensors. Additionally, at 304 the controller 144 may activate, energize, and/or maintain activation of at least one of the locks 114, 116 described above. In particular, at 304 the controller 144 may control at least one of the locks 114, 116 to maintain the mass 112 substantially stationary relative to the frame 102. In some examples, the mass 112 may be maintained at a location along the first and second guides 108, 110 such that the bottom surface A of the mass 112 is separated from the top surface B of the modulator 128 by a distance and/or height H.

At 306, the controller 144 may activate and/or energize at least one of the locks 132, 134 associated with the carrier 126 such that at least one of the locks 132, 134 may apply a counterforce to the carrier 126. For example, at 306 the controller 144 may operate at least one of the locks 132, 134 to apply a magnetic counterforce to the carrier 126 in the direction of arrow 142. Such a magnetic counterforce may be greater than or substantially equal to a total weight of the carrier 126, the modulator 128 disposed on the carrier 126, the at least one anvil 146(3) connected to the carrier 126, and/or other components of the system 100 movably connected to the carrier 126. Such a magnetic counterforce applied to the carrier 126 at 306 may temporarily maintain the carrier 126 at a substantially stationary location along the first and second guides 122, 124.

At 308, the controller 144 may operate at least one of the first and second locks 114, 116 to disengage, thereby releasing the mass 112. Releasing the mass 112 at 308 may cause the mass 112 to move in the direction of arrow 118 along at least one of the first and second guides 108, 110 due to the force of gravity. The mass 112 may travel along at least one of the first and second guides 108, 110 substantially unimpeded until the bottom surface A of the mass 112 impacts the top surface B of the modulator 128. Thus, releasing the mass 112 at 308 may cause an impact between the mass 112 disposed opposite the carrier 126, and the modulator 128 disposed on the carrier 126.

At 310, one or more of the sensors associated with the system 100 may determine the impact between the mass 112 and the modulator 128. Additionally or alternatively, at 310 at least one of the sensors associated with the system 100 may determine a position of the mass 112 relative to the modulator 128, at least one of the first and second guides 108, 110, and/or one or more other components of the system 100. For example, the force sensor 130 may detect the presence of and/or a relatively sudden increase in a force being applied to the modulator 128 as the mass 112 impacts the modulator 128. At 310, the force sensor 130 may generate a signal indicative of such a force, and may provide the generated signal to the controller 144 for processing. Additionally or alternatively, at 310 the position sensor 140 may determine a position of the mass 112 as the mass 112 approaches the modulator 128 and/or as the mass 112 impacts the modulator 128. For example, the position sensor 140 may be configured to detect when the mass 112 has traveled such that the bottom surface A is within inches, centimeters, or millimeters (or a fraction thereof) of the top surface B. Alternatively, the position sensor 140 may be configured to detect when the mass 112 has traveled such that the bottom surface A has contacted the top surface B. The position sensor 140 may generate a signal indicative of such a position of the mass 112, and may provide the generated signal to the controller 144 for processing.

At 312, the controller 144 may operate and/or otherwise control at least one of the first and second locks 132, 134 to discontinue application of the counterforce being applied to the carrier 126 at least partly in response to detecting at least one of the position of the mass 112 and/or the impact between the mass 112 and the modulator 128. For example, at 312 the controller 144 may control at least one of the locks 132, 134 to disengage the carrier 126 in response to a signal received from the force sensor 130 and/or from the position sensor 140. In examples in which at least one of the locks 132, 134 comprises an electromagnet or other device configured to apply a magnetic counterforce to the carrier 126 in the direction of arrow 142, the controller 144 may reverse a polarity of the current being directed to such an electromagnet at 312 and/or may temporarily discontinue the flow of an electrical current to the electromagnet at 312 in order to discontinue application of the counterforce. Once the counterforce is discontinued at 312, the carrier 126, the modulator 128, and the at least one anvil 146(3) connected to the carrier 126 may be free to travel in the direction of arrow 118. In particular, at 312 the counterforce applied to the carrier 126 may be discontinued at substantially the instant in time at which the mass 112 impacts the modulator 128. In further examples, at 312 the counterforce applied to the carrier 126 may be discontinued immediately prior to (e.g., one or more milliseconds before) contact between the bottom surface A of the mass 112 and the top surface B of the modulator 128.

The impact described above between the mass 112 and the modulator 128 may cause the carrier 126, the modulator 128, and the anvil 146(3) connected to the carrier 126 to move in the direction of arrow 118 toward the sample S. In particular, such impact may cause the anvil 146(3) to breach, puncture, deform, shatter, break, and/or otherwise render the sample S inoperable. In examples in which the sample S comprises a substantially planar sheet of glass, such impact may result in failure of the sample S, and such failure may be characterized by at least partial cracking, shattering, fracturing, and/or breaking of the glass.

At 314, the position sensor 136 may determine, among other things, a displacement of the carrier 126 caused by the impact between the mass 112 and the modulator 128. In particular, the sensor 136 may determine displacement of the carrier 126 from the instant at which the bottom surface A of the mass 112 contacts the top surface B of the modulator 128 until after failure of the sample S. Accordingly, the sensor 136 may determine, in real time, the displacement of the carrier 126 as the carrier 126 moves in the direction of arrow 118. In some examples, the sensor 136 may determine, for example, the displacement of the carrier 126 before, during, and after failure of the sample S. In such examples, the sensor 136 may generate signals indicative of such displacement and may provide such signals to the controller 144. The controller 144 may, in response, correlate such information with information received from various other sensors of the system 100 to determine, among other things, a displacement of the carrier 126 corresponding to failure of the sample S. For example, such a determined displacement may comprise the measured displacement of the carrier 126 at the point in time in which the sample S fails (e.g., the displacement of the carrier 126 at a failure point of the sample S). Such a determined displacement may also comprise the measured displacement of the carrier 126 corresponding to the force applied to the sample S by the anvil 146(3) causing failure of the sample S (e.g., a "failure force"). Such a failure force may comprise, for example, a maximum force applied to the sample S by the anvil 146(3) prior to failure of the sample S. In some examples, the failure force may be the force at which failure of the sample S occurs (e.g., the force at the failure point of the sample S).

At 314, the force sensor 130 may determine the force applied to the modulator 128 by the mass 112 and resulting in failure of the sample S. For example, similar to the displacement determination described above with respect to the sensor 136, the sensor 130 may determine the amount of force applied to modulator 128 and/or the carrier 126 from the instant at which the bottom surface A of the mass 112 contacts the top surface B of the modulator 128 until after failure of the sample S. Accordingly, the sensor 130 may determine, in real time, the increase and/or relative decrease in force applied to the modulator 128 by the mass 112 throughout the impact. In some examples, the sensor 130 may determine, for example, the impact force applied to the modulator 128 and/or the carrier 126 before, during, and after failure of the sample S. In such examples, the sensor 130 may generate signals indicative of such force and may provide such signals to the controller 144. The controller 144 may, in response, correlate such information with information received from various other sensors of the system 100, such as the sensor 136, to determine, among other things, the failure force described above.

At 314, the controller 144 may store the information received from the various sensors 130, 136, 140 in a memory thereof. Additionally, as will be described below, the controller 144 may correlate such information in a variety of ways in order to determine various additional information useful in determining the dynamic strength, dynamic modulus, and/or other dynamic properties of the sample S.

In some examples, it may be desirable to prevent multiple impacts between the mass 112 and the modulator 128. Accordingly, at 316 the controller 144 may utilize one or more inputs from the various sensors of the system 100 to detect at least one of the position of the mass 112 and a first impact between the mass 112 and the modulator 128. Such inputs may include, for example, a signal provided to the controller 144 by the sensor 140 indicative of the position of the mass 112. Additionally and/or alternatively, such inputs may include a signal provided to the controller 144 by the force sensor 130 indicating impact between the mass 112 and the modulator 128. At 316, the controller 144 may control the mechanism 138 to apply a counterforce to the mass 112 at least partly in response to detection of and/or determining at least one of the position of the mass 112, and the first impact between the mass 112 and the modulator 128. As noted above, the counterforce applied to the mass 112 by the mechanism 138 may be applied in the direction of arrow 142, and such a counterforce may be greater than or substantially equal to a weight of the mass 112.

Figure 4:
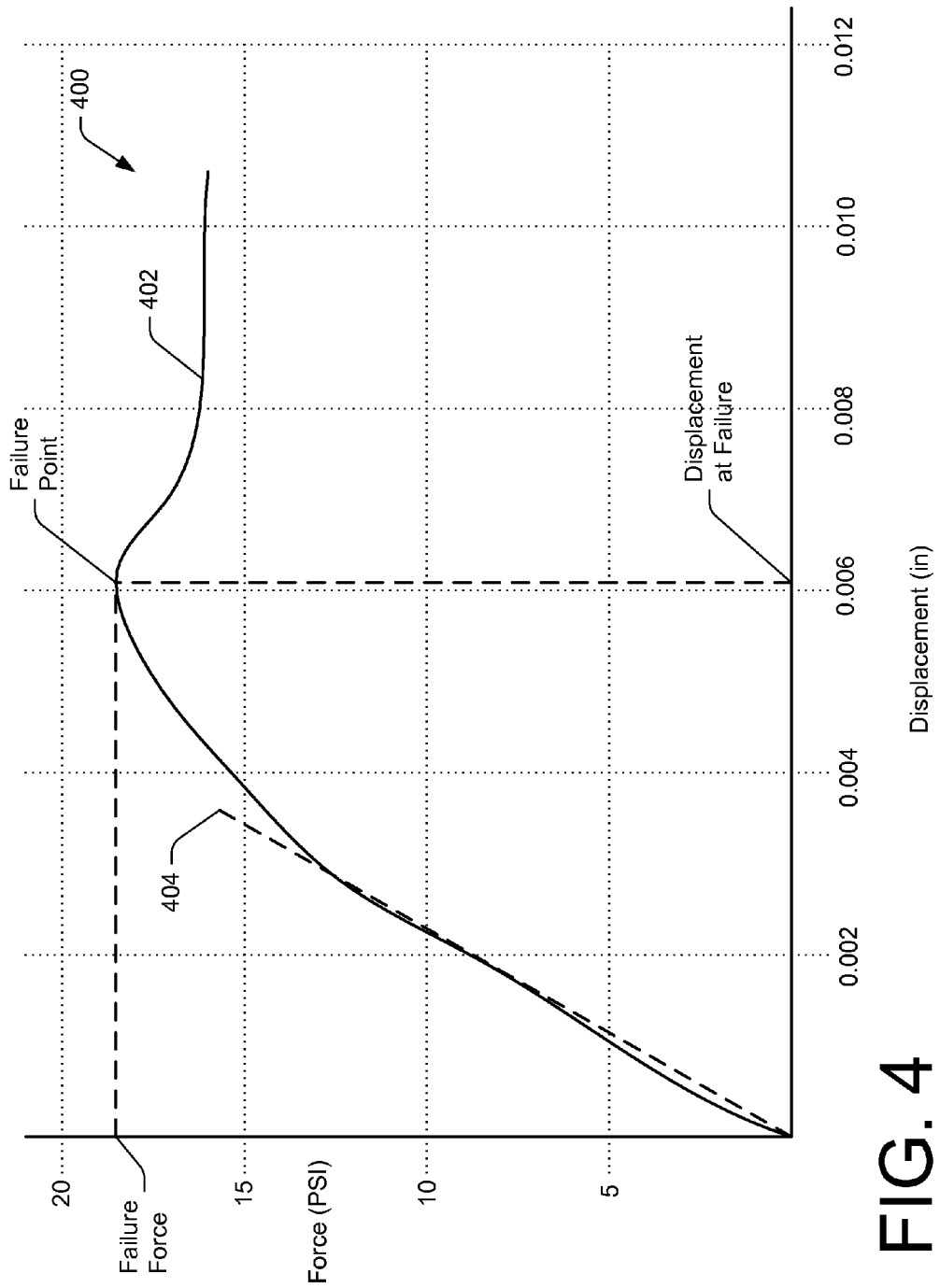
FIG. 4 illustrates an example force vs. displacement curve corresponding to a particular sample.

At 318, the controller 144 may determine at least one of a dynamic strength of the sample S and a dynamic modulus of the sample S. For example, as shown in the example plot 400 of FIG. 4 the controller 144 may generate and/or otherwise determine a relationship between the impact force and carrier displacement determined at 314. In some examples, the controller 144 may generate a force vs. displacement curve 402 corresponding to each respective sample S tested using the system 100. In addition, the controller may generate a force vs. displacement curve 402 corresponding to respective modulators 128 utilized for repeated sample testing, and each respective modulator 128 may be characterized by, for example, a different respective strain rate (s/sec).

In particular, the different strain rates of the various modulators 128 utilized in such testing may be selected in order to vary the observed relationship illustrated by the force vs. displacement curve 402. Thus, by repeating one or more of steps 302-318, using substantially similar samples S of a common material (e.g., glass), but by varying the modulator 128 employed, and thus, varying the strain rate utilized in the testing, the controller 144 may generate a plurality of curves 402. Each respective force vs. displacement curve 402 may illustrate a unique failure force, a unique displacement at failure, and a unique best-fit line 404 indicative of the increase in force and displacement during impact. For example, each best-fit line 404 may have a unique respective slope (m) associated therewith. Additionally, the failure force, displacement at failure, and best-fit line 404 illustrated by each respective force vs. displacement curve 402 may correspond to the strain rate of the modulator 128 used during testing. In this way, the controller 144 may determine at least one of a dynamic strength of the sample S, a dynamic modulus of the sample S, and/or other dynamic properties of the sample S at 318 as a function of strain rate. In such examples, the dynamic strength of the sample S determined by the controller 144 at 318 may be based on the force applied to the modulator 128 by the mass 112 at impact, and on the strain rate associated with the particular modulator 128 utilized during testing. Additionally, in such examples the dynamic modulus of the sample S determined by the controller 144 at 318 may be based on the force applied to the modulator 128 by the mass 112, the displacement of the carrier 126 determined by the sensor 136, and the strain rate associated with the modulator 128.

For example, the dynamic strength (e.g., the dynamic yield strength) of a sample S at a particular strain rate may be determined by the controller 144 at 318 based on the following equation or relationship:

$$\sigma(\epsilon) = 3FL/WT^2$$

where F represents the failure force described above and illustrated in FIG. 4; L represents the horizontal distance between peaks of the anvils 146(1), 146(2) illustrated in FIG. 1; W represents the width of the sample S illustrated in FIG. 1, and T represents the thickness of the sample S illustrated in FIG. 1. Additionally, the dynamic modulus (e.g., the dynamic Young's modulus) of a sample S at a particular strain rate may be determined by the controller 144 at 318 based on the following equation or relationship:

$$M(\epsilon) = mL^3/4WT^3$$

where m represents the slope of the best-fit line 404 described above and illustrated in FIG. 4; L represents the horizontal distance between peaks of the anvils 146(1), 146(2) illustrated in FIG. 1; W represents the width of the sample S illustrated in FIG. 1, and T represents the thickness of the sample S illustrated in FIG. 1.

As noted above, the various relationships described herein may be utilized by the controller 144 to determine a dynamic strength (e.g., a dynamic yield strength), a dynamic modulus (e.g., a dynamic Young's modulus), and/or other dynamic properties of a material as a function of strain rate. As a result, by repeating one or more of steps 302-318 using substantially similar samples S of a common material, but by varying the modulator 128 employed during each cycle, and thus, varying the strain rate utilized in the testing, the controller 144 may determine a dynamic strength of the material at each respective strain rate, and may also determine a dynamic modulus of the material at each respective strain rate. It is understood that, in further examples, the above equations may differ depending on the type of bending test being performed. For example, while the above dynamic strength and dynamic modulus equations may be appropriate for the three point bending tests described with respect to the system 100 of FIG. 1, in further examples in which two-point or four-point bending tests are performed, different dynamic strength and dynamic modulus equations may be employed. Additionally, in examples in which the system 100 is used to perform a ball-on-ring test, a ring-on-ring test, or other like test, still further dynamic strength and dynamic modulus equations may be used. It is also understood that in still further embodiments, any of the dynamic strength and dynamic modulus determinations described herein may be performed empirically. Such empirical determinations may be performed without using one or more of the equations described herein and, instead, may be accomplished through repeated testing and analysis of different samples S.

Figure 5:
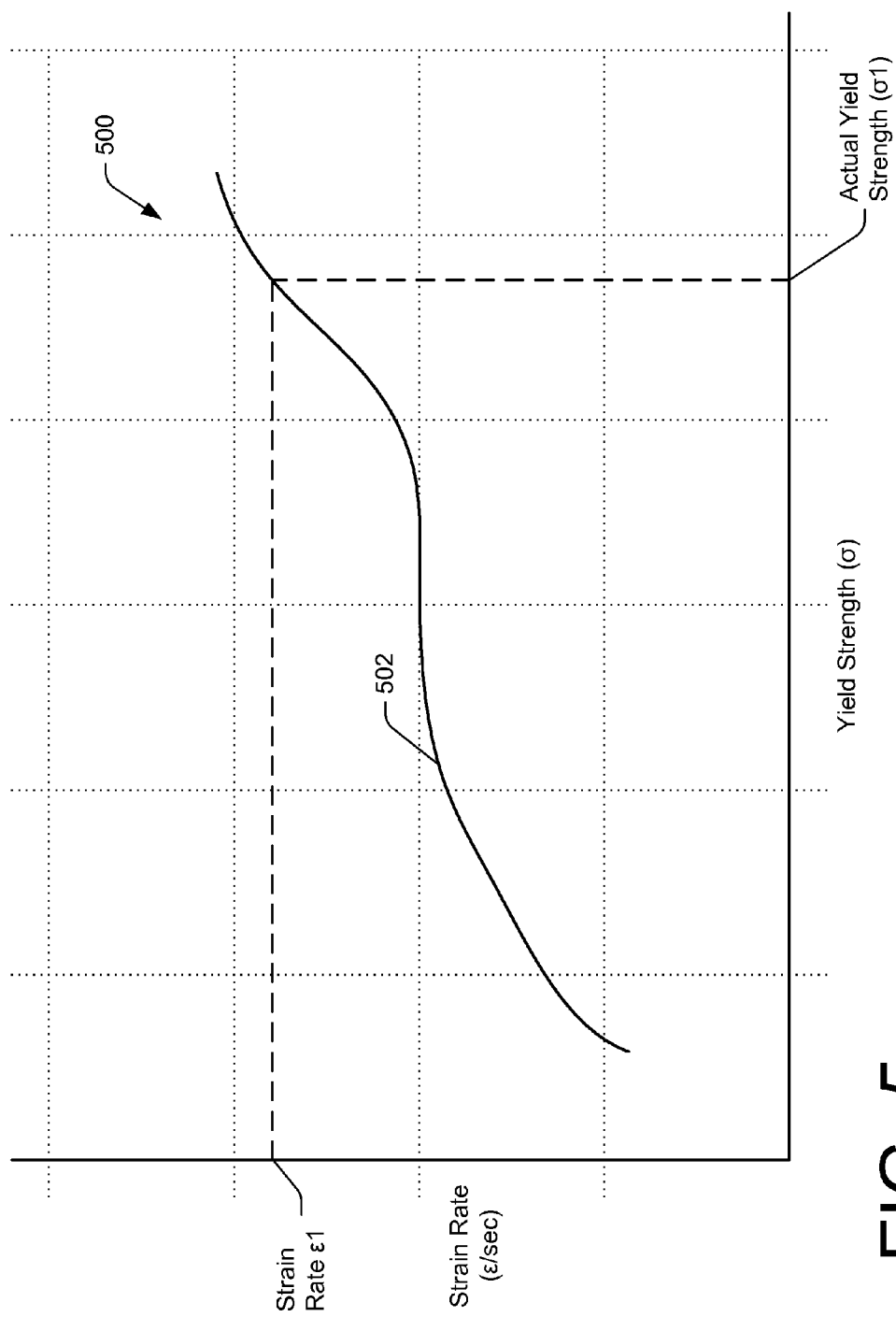
FIG. 5 illustrates an example strain rate vs. yield strength curve corresponding to a plurality of samples.
Figure 6:
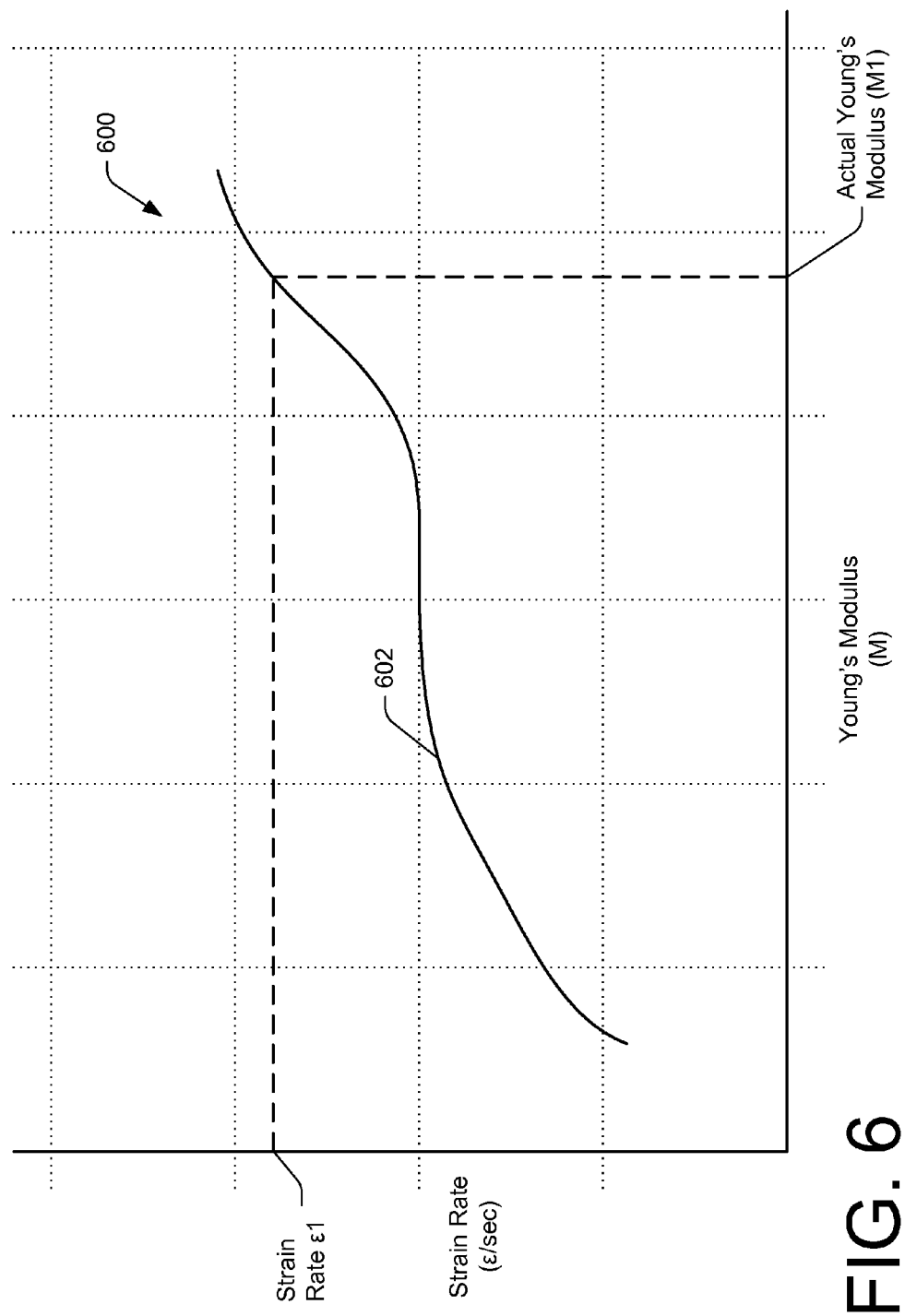
FIG. 6 illustrates an example strain rate vs. Young's modulus curve corresponding to a plurality of samples.

The plot 500 of FIG. 5 illustrates an example strain rate vs. yield strength curve 502 corresponding to a plurality of samples tested using the methods described herein. As shown in FIG. 5, a user and/or the controller 144 may determine an actual dynamic yield strength ($\sigma_1$) of a material corresponding to a given strain rate ($\epsilon_1$) using the relationship indicated by the strain rate vs. yield strength curve 502. Likewise, the plot 600 of FIG. 6 illustrates an example strain rate vs. Young's Modulus curve 602 corresponding to a plurality of samples tested using the methods described herein. As shown in FIG. 6, a user and/or the controller 144 may determine an actual dynamic Young's Modulus ($M_1$) corresponding to a given strain rate ($\epsilon_1$) using the relationship indicated by the strain rate vs. Young's Modulus curve 602.

Figure 7:
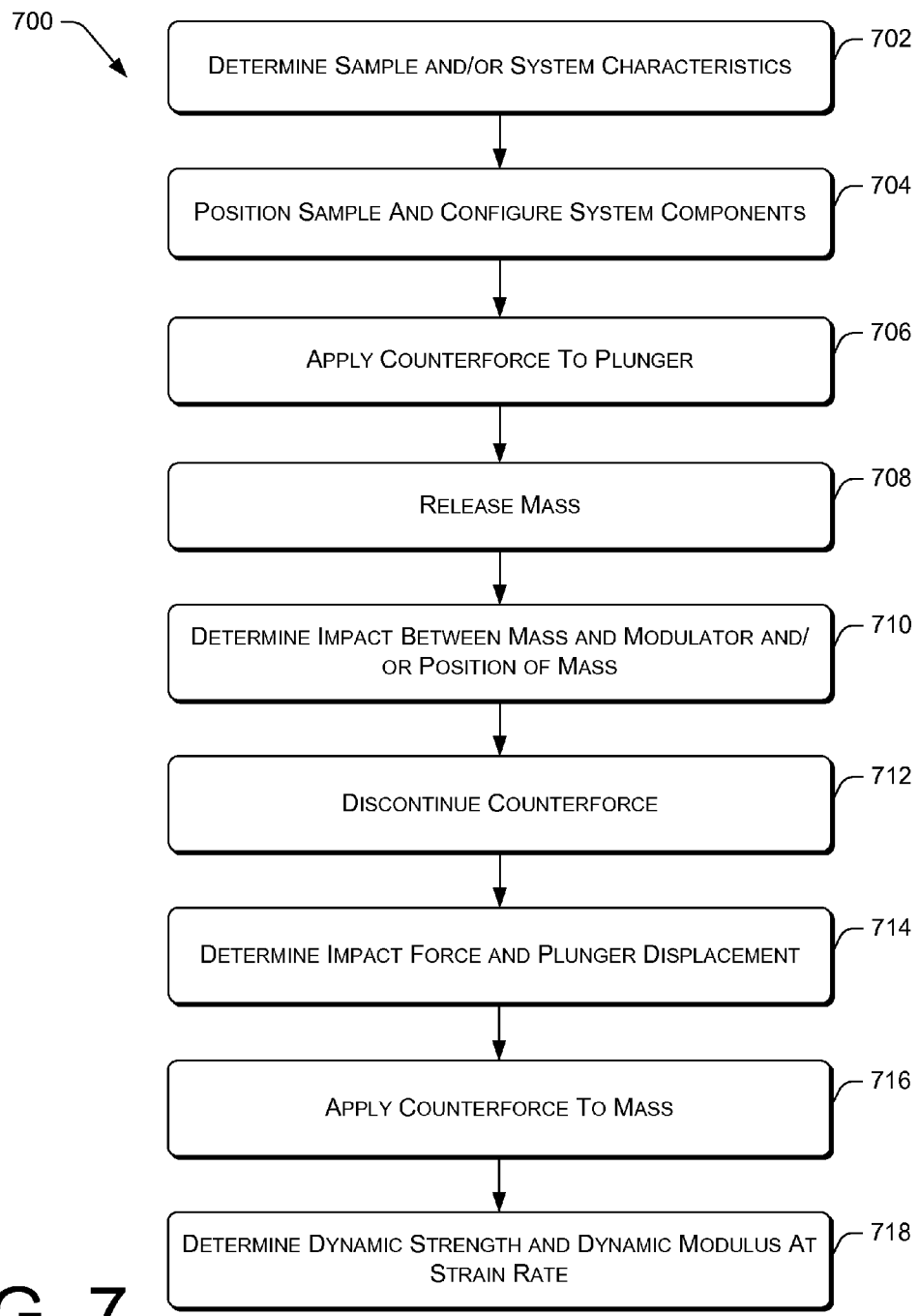
FIG. 7 illustrates a flow diagram of another example method for determining one or more dynamic properties of a sample.

FIG. 7 illustrates a flow diagram of another example method 700 of determining one or more dynamic properties and/or parameters of a sample of material. In some instances, the method 700, or portions thereof, may be substantially similar to and/or identical to corresponding portions of the method 300 described above with respect to FIGS. 3-6. Accordingly, various portions of the method 700 will be described briefly below for clarity. It is understood, however, that any of the descriptions of the method 300 described herein may be equally applicable to the example method 700 shown in FIG. 7. Additionally, one or more of the processes described above with respect to the example method 300 may be included in the example method 700 and vice versa. For purposes of the method 700, and for ease of description, a sample S comprising a battery including an outer casing, such as a rechargeable battery utilized as a power source in a wireless phone, tablet computer, electronic book reader, laptop computer, and/or other electronic device will be described unless otherwise noted. Additionally, the method 700 will be described with reference to the example system 200 of FIG. 2 unless otherwise specified.

At 702, the method 700 includes determining at least one sample and/or system characteristic. For example, as part of determining a dynamic strength of an outer casing of the battery sample S, a dynamic modulus of the casing, and/or other like dynamic property of a material included in the outer casing of the battery sample S, a user of the system 200 may calculate, measure, and/or otherwise determine at least one of the width W, thickness T, length, weight, composition, durometer, and/or other characteristics of the sample S generally, and/or of the outer casing of the battery sample S. At 702, the user may also determine the weight of the mass 112, the composition and/or strain rate (s/sec) of the modulator 128, and/or other system characteristics.

At 704, the user may position the battery sample S at a desired location relative to one or more components of the system 200 and may configure various components of the system 200 to assist in determining one or more of the dynamic properties described above. For example, the user may position the sample S such that the outer casing of the sample S is disposed within the internal space 212 of the test enclosure 202. As shown in FIG. 2, the sample S may be disposed in a substantially horizontal orientation on the base 206 of the test enclosure 202. In alternative examples, the sample S may be disposed in a substantially vertical orientation (e.g., substantially perpendicular to the orientation illustrated in FIG. 2) on the base 206. Additionally, at 704, the tip 218 of the plunger 216 may be positioned proximate, adjacent to, and/or abutting a top surface E of the sample S. In such examples, at least part of the plunger 216 may extend from within the internal space 212 to a location external to the test enclosure 202. Additionally, the plunger 216 may be movable relative to the test enclosure, such as via the passage 214, in the direction of arrow 118 toward the sample S and/or toward the base 206.

At 704, the user may also activate and/or energize one or more of the sensors described above. For example, the force sensor 130, the position sensor 136, and/or the position sensor 140 may be activated at 704 in order to measure, calculate, sense, and/or otherwise determine the various operating characteristics of the system 200 described above with respect to such sensors. Additionally, at 704 the controller 144 may activate, energize, and/or maintain activation of at least one of the locks 114, 116 described above. In particular, at 304 the controller 144 may control at least one of the locks 114, 116 to maintain the mass 112 substantially stationary relative to the frame 102.

At 706, the controller 144 may activate and/or energize the lock 132 associated with the plunger 216 such that the lock 132 may apply a counterforce to the plunger 216. For example, at 706 the controller 144 may operate the lock 132 to apply a counterforce to the plunger 216 in the direction of arrow 142. Such a magnetic counterforce may be greater than or substantially equal to a total weight of the plunger 216, the modulator 128 disposed on the plunger 216, and/or other components of the system 200 movably connected to the plunger 216. Such a magnetic counterforce applied to the plunger 216 at 706 may temporarily maintain the plunger 216 at a substantially stationary location relative to the test enclosure 202 and/or the sample S.

At 708, the controller 144 may operate at least one of the first and second locks 114, 116 to disengage, thereby releasing the mass 112. Releasing the mass 112 at 708 may cause the mass 112 to move in the direction of arrow 118 along at least one of the first and second guides 108, 110 due to the force of gravity. The mass 112 may travel along at least one of the first and second guides 108, 110 substantially unimpeded until the bottom surface A of the mass 112 impacts the top surface B of the modulator 128. Thus, releasing the mass 112 at 308 may cause an impact between the mass 112 disposed opposite the plunger 216 and the modulator 128 connected to the plunger 216 external to the test enclosure 202.

At 710, one or more of the sensors associated with the system 200 may determine the impact between the mass 112 and the modulator 128. Additionally or alternatively, at 710 at least one of the sensors associated with the system 200 may determine a position of the mass 112 relative to the modulator 128, at least one of the first and second guides 108, 110, and/or one or more other components of the system 200. For example, the force sensor 130 may detect the presence of and/or a relatively sudden increase in a force being applied to the modulator 128 as the mass 112 impacts the modulator 128. At 710, the force sensor 130 may generate a signal indicative of such a force, and may provide the generated signal to the controller 144 for processing. Additionally or alternatively, at 710 the position sensor 140 may determine a position of the mass 112 as the mass 112 approaches the modulator 128 and/or as the mass 112 impacts the modulator 128. The position sensor 140 may generate a signal indicative of such a position of the mass 112, and may provide the generated signal to the controller 144 for processing.

At 712, the controller 144 may operate and/or otherwise control the lock 132 to discontinue application of the counterforce being applied to the plunger 216 at least partly in response to detecting at least one of the position of the mass 112 and/or the impact between the mass 112 and the modulator 128. For example, at 712 the controller 144 may control the lock 132 to disengage the plunger 216 at least partly in response to a signal received from the force sensor 130 and/or from the position sensor 140. Once the counterforce is discontinued at 712, the plunger 216 and the modulator 128 may be free to travel in the direction of arrow 118. In particular, at 712 the counterforce applied to the plunger 216 may be discontinued at substantially the instant in time at which the mass 112 impacts the modulator 128. In further examples, at 712 the counterforce applied to the plunger 216 may be discontinued immediately prior to (e.g., one or more milliseconds before) contact between the bottom surface A of the mass 112 and the top surface B of the modulator 128.

Impact described above between the mass 112 and the modulator 128 may cause the plunger 216 and the modulator 128 to move in the direction of arrow 118 toward the sample S. In particular, such impact may cause the tip 218 of the plunger 216 to breach, puncture, deform, shatter, and/or otherwise break the outer casing of the battery sample S. In examples in which the sample S comprises a battery sample, such impact may result in failure of the sample S and/or of the outer casing, and such failure may be characterized by at least one of breaching, puncturing, piercing, deformation, shattering, and/or otherwise breaking of the outer casing. Such failure may also be characterized and/or determined by a signal from one or more of the sensors 226 indicating that the battery sample S is no longer capable of storing a charge and/or discharging electrical power stored therein.

At 714, the position sensor 136 may determine, among other things, a displacement of the plunger 216 caused by the impact between the mass 112 and the modulator 128. In particular, the sensor 136 may determine displacement of the plunger 216 from the instant at which the bottom surface A of the mass 112 contacts the top surface B of the modulator 128 until after failure of the casing of the battery sample S. Accordingly, the sensor 136 may determine, in real time, the displacement of the plunger 216 as the plunger 216 moves in the direction of arrow 118. In some examples, the sensor 136 may determine, for example, the displacement of the plunger 216 before, during, and after failure of the casing of the sample S. In such examples, the sensor 136 may generate signals indicative of such displacement and may provide such signals to the controller 144. The controller 144 may, in response, correlate such information with information received from various other sensors of the system 200 to determine, among other things, a displacement of the plunger 216 corresponding to failure of the sample S. For example, such a determined displacement may comprise the measured displacement of the plunger 216 at the point in time in which the sample S and/or the outer casing of the sample S fails (e.g., the displacement of the plunger 216 at a failure point of the casing). Such a determined displacement may also comprise the measured displacement of the plunger 216 corresponding to the force applied to the sample S by the plunger 216 causing failure of the sample S. As similarly noted above with respect to the method 300 of FIG. 3, such a failure force may comprise, for example, a maximum force applied to the sample S by the plunger 216 prior to failure of the sample S and/or of the casing. In some examples, the failure force may be the force at which failure of the casing occurs (e.g., the force applied at the failure point of the casing).

At 714, the force sensor 130 may determine the force applied to the modulator 128 by the mass 112 and the resulting in failure of the sample S. For example, similar to the displacement determination described above with respect to the sensor 136, the sensor 130 may determine the amount of force applied to modulator 128 and/or the plunger 216 from the instant at which the bottom surface A of the mass 112 contacts the top surface B of the modulator 128 until after failure of the sample S and/or of the casing. Accordingly, the sensor 130 may determine, in real time, the increase and/or relative decrease in force applied to the modulator 128 by the mass 112 throughout the impact. The sensor 130 may generate signals indicative of such force and may provide such signals to the controller 144. The controller 144 may, in response, correlate such information with information received from various other sensors of the system 200, such as the sensor 136, to determine, among other things, the failure force described above.

At 714, the controller 144 may store the information received from the various sensors 130, 136, 140 in a memory thereof. Additionally, as will be described below, the controller 144 may correlate such information in a variety of ways in order to determine various additional information useful in determining the dynamic strength, dynamic modulus, and/or other dynamic properties of the sample S and/or of the outer casing.

In some examples, it may be desirable to prevent multiple impacts between the mass 112 and the modulator 128. Accordingly, at 716 the controller 144 may utilize one or more inputs from the various sensors of the system 200 to detect at least one of the position of the mass 112 and a first impact between the mass 112 and the modulator 128. Such inputs may include, for example, a signal provided to the controller 144 by the sensor 140 indicative of the position of the mass 112. Additionally and/or alternatively, such inputs may include a signal provided to the controller 144 by the force sensor 130 indicating impact between the mass 112 and the modulator 128. At 716, the controller 144 may control the mechanism 138 to apply a counterforce to the mass 112 at least partly in response to detection of and/or determining at least one of the position of the mass 112 and the first impact between the mass 112 and the modulator 128. As noted above, the counterforce applied to the mass 112 by the mechanism 138 may be applied in the direction of arrow 142, and such a counterforce may be greater than or substantially equal to a weight of the mass 112.

At 718, the controller 144 may determine at least one of a dynamic strength of the outer casing of the sample S and a dynamic modulus of the outer casing of the sample S. For example, the controller 144 may generate and/or otherwise determine a relationship between the impact force and plunger displacement determined at 714. In some examples, the controller 144 may generate a force vs. displacement curve (substantially similar to the curve 402 shown in FIG. 4) corresponding to each respective sample S tested using the system 200. In addition, the controller 144 may generate a force vs. displacement curve (substantially similar to the curve 402 shown in FIG. 4) corresponding to respective modulators 128 utilized for repeated sample testing, and each respective modulator 128 may be characterized by, for example, a different respective strain rate (s/sec). Each respective force vs. displacement curve may illustrate a unique failure force, a unique displacement at failure, and a unique best-fit line indicative of the increase in force and displacement during impact. In this way, the controller 144 may determine at least one of a dynamic strength of the outer casing of the battery sample S, a dynamic modulus of the outer casing, and/or other dynamic properties of the sample S at 718 as a function of strain rate. In such examples, the dynamic strength determined by the controller 144 at 718 may be based on the force applied to the modulator 128 by the mass 112 at impact, and on the strain rate associated with the particular modulator 128 utilized during testing. Additionally, in such examples the dynamic modulus determined by the controller 144 at 718 may be based on the force applied to the modulator 128 by the mass 112, the displacement of the plunger 216 determined by the sensor 136, and the strain rate associated with the modulator 128.

As noted above, the various relationships described herein may be utilized by the controller 144 to determine a dynamic strength (e.g., a dynamic yield strength), a dynamic modulus (e.g., a dynamic Young's modulus), and/or other dynamic properties of a material as a function of strain rate. In particular, in the example system 200 described with respect to FIG. 2, the controller 144 may determine a dynamic strength ($\sigma(\epsilon)$) of the outer casing of a battery pack or other battery sample as a function of at least the strain rate of the modulator 128 and the force applied to the modulator 128 or other such piece of material at the failure point of the outer casing. The dynamic strength of the outer casing may also be determined based on a thickness of the outer casing and/or other variables. In still further embodiments, the dynamic strength of the outer casing may be determined empirically, such as through repeated testing and analysis of different battery samples S. Additionally, the controller 144 may determine a dynamic modulus ($M(\epsilon)$) of the outer casing as a function of at least the strain rate of the modulator and the displacement of the plunger 136 at the failure point. The dynamic modulus of the outer casing may also be determined based on the thickness of the outer casing and/or other variables. In still further embodiments, the dynamic modulus of the outer casing may be determined empirically, such as through repeated testing and analysis of different battery samples S. In additional examples in which the battery pack and/or other sample S described herein with respect to FIG. 2 is disposed on one or more anvils 146 or other supports during testing, however, the controller 144 may employ the equations described above with respect to the system 100 of FIG. 1 to determine the dynamic strength $\sigma(\epsilon)$ and the dynamic modulus $M(\epsilon)$ of the outer casing. As a result, by repeating one or more of steps 702-718 using substantially similar samples S of a common material, but by varying the modulator 128 employed during each cycle, and thus, varying the strain rate utilized in the testing, the controller 144 may determine a dynamic strength of the material at each respective strain rate, and may also determine a dynamic modulus of the material at each respective strain rate. It is understood that in still further examples, the determination of dynamic strength and/or dynamic modulus of the outer casing may not be required, and in such examples, step 718 may be omitted. Further, in any of the examples described herein, the dynamic strength and/or dynamic modulus of the outer casing of the battery sample S may be determined without actual piercing, puncturing, and/or failure of the outer casing. For example, the dynamic strength of the outer casing may be determined based on the maximum force applied to the modulator 128 by the mass 112 at impact, and on the strain rate associated with the particular modulator 128 utilized during testing, even if such impact does not puncture the outer casing. Additionally, in such examples the dynamic modulus may be determined based on the maximum displacement of the plunger 216 determined by the sensor 136 at impact, and the strain rate associated with the modulator 128, even if such impact does not puncture the outer casing.

Figure 8:
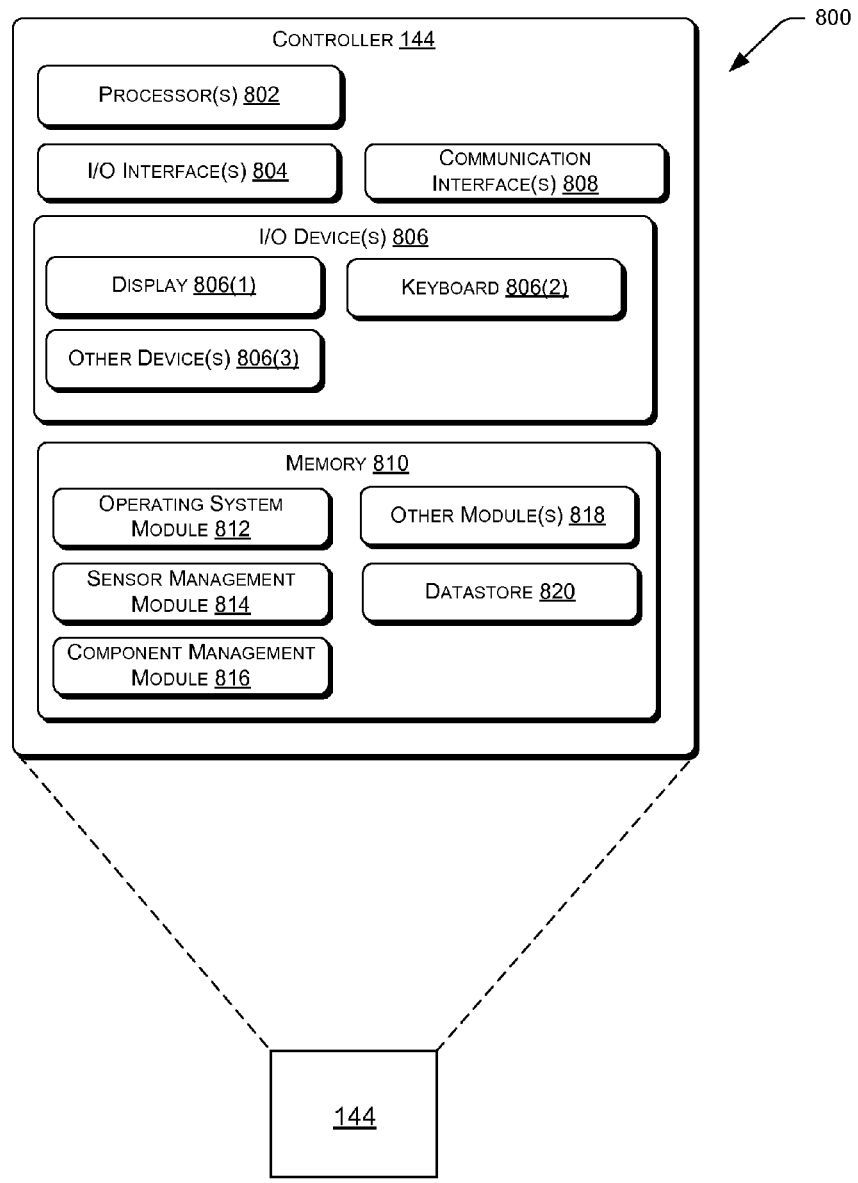
FIG. 8 is a schematic diagram illustrating an example controller of the present disclosure.

FIG. 8 is a block diagram 800 of the controller 144. The controller 144 may include one or more processors 802 configured to execute stored instructions. The processors 802 may comprise one or more cores. The controller 144 may include one or more input/output ("I/O") interface(s) 804 to allow the controller 144 to communicate with other devices. The I/O interfaces 804 may comprise inter-integrated circuit ("12C"), serial peripheral interface bus ("SPI"), universal serial bus ("USB"), RS-232, media device interface, and so forth.

The I/O interface(s) 804 may couple to one or more I/O devices 806. The I/O device(s) 806 may include one or more displays 806(1), keyboards 806(2), mice, touchpads, touchscreens, and/or other such devices 806(3). The one or more displays 806(1) may be configured to provide visual output to the user. For example, the displays 806(1) may be connected to the processor(s) 802 and may be configured to render and/or otherwise display content thereon. For example, the plots described above with respect to FIGS. 4-6 may be displayed on the display 806(1).

As noted above, each of the various sensors 130, 136, 140, 226 described herein may be coupled to the controller 144 and, in particular, such sensors 130, 136, 140, 226 may be coupled to the one or more processor(s) 802. The processor(s) 802 may be configured to control and receive input from the sensors 130, 136, 140, 226 to determine the force applied to the modulator 128, the displacement of the carrier 126, the displacement of the plunger 216, and so forth. Further, the processor(s) 802 may control operation of the locks 114, 116, 132, 134, counterforce mechanisms 138, pumps 222, and/or other components of the systems 100, 200 described herein based at least partly on inputs received from the sensors 130, 136, 140, 226. The processor(s) 802 may also be configured to determine the dynamic strength, dynamic modulus, and other parameters described herein based at least partly on inputs received from the sensors 130, 136, 140, 226.

The controller 144 may also include one or more communication interfaces 808 configured to provide communications between the controller 144 and other devices, as well as between the controller 144 and various components of the systems 100, 200. Such communication interface(s) 808 may be used to connect to one or more personal area networks ("PAN"), local area networks ("LAN"), wide area networks ("WAN"), and so forth. For example, the communications interfaces 808 may include radio modules for a WiFi LAN and a Bluetooth PAN. The controller 144 may also include one or more busses or other internal communications hardware or software that allow for the transfer of data between the various modules and components of the controller 144.

As shown in FIG. 8, the controller 144 includes one or more memories 810. The memory 810 comprises one or more non-transitory computer-readable storage media ("CRSM"). The CRSM may be anyone or more of an electronic storage medium, a magnetic storage medium, an optical storage medium, a quantum storage medium, a mechanical computer storage medium and so forth. The memory 810 provides storage of computer readable instructions, data structures, program modules and other data for the operation of the controller 144. The memory 810 may be connected to the processor(s) 802, and may store inputs received from the sensors 130, 136, 140, 226.

The memory 810 may include at least one operating system (OS) module 812. The OS module 812 is configured to manage hardware resources such as the I/O interfaces 804 and provide various services to applications or modules executing on the processors 802. Also stored in the memory 810 may be a sensor management module 814, a component management module 816, and other modules 818. The sensor management module 814 is configured to provide for control and adjustment of the various sensors 130, 136, 140, 226 described herein. Likewise, the component management module 816 is configured to provide for control and adjustment of the individual components of systems 100, 200 coupled to the controller 144. The component management module 816 may be configured to respond to one or more signals from the processor(s) 802 and/or from one or more of the sensors 130, 136, 140, 226. These signals may be indicative of the parameters described above. Other modules 818 may be stored in the memory 810. For example, a rendering module may be configured to process inputs and/or for presentation on the display. Additionally, a computation module may be configured to assist the processor(s) 802 in calculating the dynamic strength, dynamic modulus, actual strength, actual modulus, and other parameters described herein.

The memory 810 may also include a datastore 820 to store information. The datastore 820 may use a flat file, database, linked list, tree, or other data structure to store the information. In some implementations, the datastore 820 or a portion of the datastore 820 may be distributed across one or more other devices including servers, network attached storage devices and so forth. The data store 820 may store information about one or more modulators 128, samples S, and so forth. Other data may also be stored in the datastore 820 such as the results of various tests performed using the systems 100, 200, and so forth.

While FIG. 8 illustrates various example components, the controller 144 may have additional features or functionality. For example, the controller 144 may also include additional data storage devices (removable and/or non-removable) such as, for example, magnetic disks, optical disks, or tape. The additional data storage media may include volatile and nonvolatile, removable and non-removable media implemented in any method or technology for storage of information, such as computer readable instructions, data structures, program modules, or other data. In addition, some or all of the functionality described in association with the controller 144 may reside remotely from the controller 144 in some implementations. In these implementations, the controller 144 may utilize the communication interface(s) 808 to communicate with and utilize this functionality.

As noted above, example embodiments of the present disclosure enable the determination of one or more dynamic properties of a sample of material. For example, the various systems 100, 200 described herein may be configured to enable the user to impact a variety of different modulators 128 with a mass 112. Such an impact may result in failure of the sample, and by measuring, among other things, the force imparted by the mass 112 to the modulator 128 and the displacement of one or more components of the systems 100, 200 associated with the modulator 128, the controller 144 of the system 100, 200 may determine a dynamic strength, dynamic modulus, and/or other dynamic properties of the sample of material.

As a result of the embodiments described herein, substantially planar samples of material may be subjected to various testing cycles in order to determine one or more such dynamic properties. In particular, substantially planar samples of brittle materials such as glass may be tested using the various systems 100, 200 described herein. Dynamic testing of such materials is difficult using known testing systems due to the fact that such known systems are not configured to stretch and/or apply other dynamic loads to such materials without risking failure. In additional example embodiments, potentially combustible and/or other potentially dangerous samples of material, such as battery samples, may be tested using the various systems 100, 200 described herein. Known systems may not be configured to protect the user from gases, particles, and/or other components jettisoned by such potentially dangerous material samples during dynamic testing, and as a result, such known systems are not acceptable in most testing environments. Accordingly, the example systems and methods of the present disclosure offer unique and heretofore unworkable approaches to dynamic material testing. Such methods improve user efficiency and improve the overall accuracy of the dynamic property determination for such materials.

CONCLUSION

Although the techniques have been described in language specific to structural features and/or methodological acts, it is to be understood that the appended claims are not necessarily limited to the features or acts described. Rather, the features and acts are described as example implementations of such techniques.

Alternate implementations are included within the scope of the examples described herein in which elements or functions may be deleted, or executed out of order from that shown or discussed, including substantially synchronously or in reverse order, depending on the functionality involved as would be understood by those skilled in the art. It should be emphasized that many variations and modifications may be made to the above-described examples, the elements of which are to be understood as being among other acceptable examples. All such modifications and variations are intended to be included herein within the scope of this disclosure and protected by the following claims.

The invention claimed is:

1. A method, comprising:
   positioning a battery pack within an internal space of a test enclosure, the battery pack including an outer casing;
   positioning a tip of a plunger proximate to a top surface of the outer casing, wherein the plunger extends from within the internal space to a location external to the test enclosure and is moveable relative to the test enclosure in a first direction toward the battery pack;
   causing a first impact between a mass disposed opposite to the plunger and a piece of material having a known strain rate coupled to the plunger, the piece of material being disposed external to the test enclosure, wherein:
      the mass is moveable in the first direction along a guide of a first frame,
      the first impact causes the plunger to move in the first direction, and
      contact between the plunger and the outer casing punctures the casing at a failure point of the outer casing;
   determining a displacement of the plunger, caused by the first impact, at the failure point of the outer casing;
   determining a force applied to the piece of material, by the mass, at the failure point of the outer casing; and
   determining a dynamic strength ($\sigma(\epsilon)$) of the outer casing or a dynamic modulus ($M(\epsilon)$) of the outer casing, wherein the dynamic strength is determined as a function of the strain rate and the force applied to the piece of material and the dynamic modulus is determined as a function of the strain rate and the displacement of the plunger.

2. The method of claim 1, further comprising:
   applying a magnetic counterforce to the plunger, wherein the counterforce immobilizes the plunger, the piece of material, and the tip relative to the test enclosure;
   detecting a position of the mass relative to the piece of material at the first impact; and
   discontinuing application of the counterforce in response to detecting the position of the mass.

3. The method of claim 1, further comprising:
   detecting a position of the mass relative to the piece of material at the first impact; and
   applying a counterforce to the mass in response to detecting the position of the mass, wherein
      the counterforce is applied in a second direction opposite the first direction, and
      the counterforce prohibits a second impact between the mass and the piece of material separate from the first impact.

4. The method of claim 1, wherein the piece of material comprises a first piece of material characterized by a first strain rate, the battery pack comprises a first battery pack, and the failure point of the outer casing comprises a first failure point, the method further comprising:
   replacing the first piece of material with a second piece of material characterized by a second strain rate different from the first strain rate;
   replacing the first battery pack with a second battery pack;
   causing a second impact between the mass and the second piece of material, wherein the second impact causes the plunger to puncture an outer casing of the second battery pack at a second failure point of the outer casing of the second battery pack;
   determining a force applied to the second piece of material, by the mass, at the second failure point of the outer casing of the second battery pack;
   determining a dynamic strength of the outer casing of the second battery pack or a dynamic modulus of the outer casing of the second battery pack, wherein the dynamic strength of the outer casing of the second battery pack and the dynamic modulus of the outer casing of the second battery pack are based on the force applied to the second piece of material and the second strain rate; and
   determining an actual strength of an outer casing material or an actual modulus of the outer casing material, wherein the actual strength is based on the dynamic strength of the outer casing of the first battery pack and the dynamic strength of the outer casing of the second battery pack, and the actual modulus is based on the dynamic modulus of the outer casing of the first battery pack and the dynamic modulus of the outer casing of the second battery pack.

5. The method of claim 1, wherein the plunger extends within the internal space via a passage of the test enclosure, the method further comprising:
   evacuating air from the internal space of the test enclosure such that a pressure within the internal space is less than an atmospheric pressure; and
   directing pressurized nitrogen into the internal space to suppress combustion resulting from the first impact.

6. A system, comprising:
   a frame including a guide and a mass movable along the guide in a first direction;
   a test enclosure disposed opposite to the mass and including a top wall, a base opposite to the top wall, a pair of sidewalls extending from the top wall to the base, and a passage formed in the top wall, the top wall, base, and pair of sidewalls defining an internal space of the test enclosure;
a plunger movably disposed within the passage and having a portion extending into the internal space;
a modulator connected to the plunger opposite to the mass, wherein
the modulator is characterized by a strain rate and is moveable with the plunger in response to an impact between the mass and the modulator,
the impact moves the plunger in the first direction and causes the plunger to contact a casing of a battery sample disposed within the internal space, and
contact between the plunger and the casing results in failure of the casing;
a first sensor configured to detect a displacement of the plunger at a point in time at which the casing fails;
a second sensor configured to determining a force applied to the modulator, by the mass, at the point in time at which the casing fails; and
a controller coupled to the first and second sensors, the controller configured to determine at least one of a dynamic strength of the casing or a dynamic modulus of the casing, wherein:
the dynamic strength is based on the force applied to the modulator and the strain rate, and
the dynamic modulus is based on the displacement of the plunger and the strain rate.

7. The system of claim 6, further comprising:
an electromagnet supported by the test enclosure and configured to selectively apply a magnetic counterforce to the plunger in a second direction opposite the first direction, wherein the counterforce immobilizes the plunger and the modulator relative to the test enclosure; and
a third sensor coupled to the controller and configured to detect a position of the mass at the point in time at which the casing fails, the controller being configured to discontinue application of the counterforce by the electromagnet at least partly in response to detection of the position of the mass.

8. The system of claim 6, further comprising:
a third sensor coupled to the controller and configured to detect at least one of a position of the mass at the point in time at which the casing fails or the impact between the mass and the modulator; and
a pull solenoid connected to the frame and configured to apply a counterforce to the mass at least partly in response to detection of the at least one of the position of the mass and the impact, wherein
the impact between the mass and the modulator comprises a first impact,
the counterforce is applied in a second direction opposite the first direction, and
the counterforce prevents a second impact between the mass and the modulator separate from the first impact.

9. The system of claim 6, further comprising a vacuum pump fluidly connected to the internal space via the passage and configured to evacuate air from the internal space of the test enclosure such that a pressure within the internal space is less than an atmospheric pressure.

10. The system of claim 6, further comprising a source of pressurized nitrogen fluidly connected to the internal space via an inlet of the test enclosure, and a flame arrestor fluidly connected to the inlet and configured to restrict fluid disposed within the internal space from exiting the test enclosure via the inlet.

11. The system of claim 6, further comprising a third sensor coupled to the battery sample and configured to determine at least one of a voltage or a temperature of the battery sample as the plunger contacts the casing.

12. The system of claim 6, further comprising at least one of a filter or a muffler fluidly connected to an outlet of the test enclosure, the at least one of the filter or the muffler configured to capture components of fluid exiting the internal space via the outlet.

13. A method, comprising:
positioning a mass at a location opposite to a top surface of a modulator, wherein the modulator is characterized by a strain rate and is support by a plunger, at least a portion of the plunger extending into an internal space of a test enclosure disposed opposite the mass, and the modulator being disposed external to the test enclosure;
releasing the mass such that the mass impacts the modulator, wherein
impact between the mass and the modulator moves the plunger in a first direction toward a battery sample disposed within the internal space,
the plunger contacts a casing of the battery sample, and
contact between the plunger and the casing results in failure of the casing;
determining a displacement of the plunger at a point in time at which the casing fails;
determining a force applied to the modulator, by the mass, at the point in time at which the casing fails; and
determining at least one of a dynamic strength of the casing or a dynamic modulus of the casing, wherein:
the dynamic strength is based on the force applied to the modulator and the strain rate, and
the dynamic modulus is based on the displacement of the plunger and the strain rate.

14. The method of claim 13, wherein releasing the mass comprises disengaging a lock configured to immobilize the mass at the location, and directing the mass to travel in the first direction along a guide of a frame supporting the mass.

15. The method of claim 13, further comprising:
applying a first counterforce to the plunger in a second direction opposite the first direction, wherein the first counterforce immobilizes the plunger and the modulator relative to the test enclosure;
detecting a position of the mass as the mass impacts the modulator;
discontinuing application of the first counterforce at least partly in response to detecting the position of the mass; and
applying a second counterforce to the mass at least partly in response to detecting the position of the mass, wherein
the second counterforce is applied in the second direction, and
the second counterforce prevents an additional impact between the mass and the modulator.

16. The method of claim 13, wherein the plunger extends into the internal space of the test enclosure via a passage formed in a top wall of the test enclosure, the method further comprising evacuating air from the internal space of the enclosure using a vacuum pump fluidly connected to the internal space via the passage such that a pressure within the internal space is less than an atmospheric pressure.

17. The method of claim 13, further comprising directing pressurized nitrogen to the internal space via an inlet of the test enclosure, and restricting fluid disposed within the internal space from exiting the test enclosure via the inlet.

18. The method of claim 13, further comprising determining at least one of a voltage or a temperature of the battery sample, with a sensor coupled to the battery sample, as the plunger contacts the casing.

19. The method of claim 13, further comprising maintaining a pressure within the internal space of the test enclosure less than or substantially equal to a threshold pressure using a relief valve fluidly connected to an outlet of the test enclosure.

20. The method of claim 13, further comprising capturing components of a flow of fluid exiting the internal space via an outlet of the test enclosure using at least one of a muffler or a filter fluidly connected to the outlet.

\* \* \* \* \*